United States Patent
Christiansen et al.

(10) Patent No.: US 9,240,043 B2
(45) Date of Patent: Jan. 19, 2016

(54) REPRODUCIBLE QUANTIFICATION OF BIOMARKER EXPRESSION

(75) Inventors: Jason Christiansen, Glastonbury, CT (US); Robert Pinard, Andover, MA (US); Mark Gustavson, Niantic, CT (US); Brian Bourke, Hamden, CT (US); Gregory R. Tedeschi, Cromwell, CT (US); Dylan M. Reilly, Middletown, CT (US); Maciej P. Zerkowski, Clinton, CT (US); Christine Williams, Middletown, CT (US); Dongxiao Wang, Orange, CT (US)

(73) Assignee: NOVARTIS AG, Basel (CH)

( * ) Notice: Subject to any disclaimer, the term of this patent is extended or adjusted under 35 U.S.C. 154(b) by 963 days.

(21) Appl. No.: 12/560,129

(22) Filed: Sep. 15, 2009

(65) Prior Publication Data

US 2010/0136549 A1 Jun. 3, 2010

Related U.S. Application Data

(60) Provisional application No. 61/097,415, filed on Sep. 16, 2008.

(51) Int. Cl.
| | |
|---|---|
| *G01N 33/48* | (2006.01) |
| *G01N 33/50* | (2006.01) |
| *G01N 31/00* | (2006.01) |
| *G06T 7/00* | (2006.01) |
| *G06F 19/12* | (2011.01) |
| *G06F 19/24* | (2011.01) |
| *G06F 19/26* | (2011.01) |
| *G06T 7/40* | (2006.01) |

(52) U.S. Cl.
CPC .............. *G06T 7/0012* (2013.01); *G06F 19/12* (2013.01); *G06F 19/24* (2013.01); *G06F 19/26* (2013.01); *G06T 7/403* (2013.01); *G06T 2207/30024* (2013.01)

(58) Field of Classification Search
None
See application file for complete search history.

(56) References Cited

U.S. PATENT DOCUMENTS

| | | |
|---|---|---|
| 1,914,322 A | 6/1933 | Bickley |
| 3,958,122 A | 5/1976 | Jowett et al. |
| 4,480,189 A | 10/1984 | Miyake et al. |

(Continued)

FOREIGN PATENT DOCUMENTS

| | | |
|---|---|---|
| EP | 0 709 667 | 5/1996 |
| EP | 0 549 905 | 4/1999 |

(Continued)

OTHER PUBLICATIONS

Rubin et al. Quantitative determination of expression of the prostate cancer protein alpha-methylacyl-CoA racemase using automated quantitative analysis (AQUA): A novel paradigm for automated and continuous biomarker measurements. American Journal of Pathology, vol. 164, 2004, pp. 831-840.*

(Continued)

*Primary Examiner* — Russell S Negin
(74) *Attorney, Agent, or Firm* — Gilberto M. Villacorta; Daniel R. Shelton; Foley & Lardner LLP

(57) ABSTRACT

A method is described for the reproducible quantification of biomarker expression, including biomarker expression in a tissue sample. Methods and systems are described whereby reproducible scores for biomarker expression are obtained independent of instrument, its location, or operator.

21 Claims, 15 Drawing Sheets

(56) References Cited

U.S. PATENT DOCUMENTS

| | | |
|---|---|---|
| 4,557,599 A | 12/1985 | Zimring |
| 4,859,062 A | 8/1989 | Thurn et al. |
| 4,892,817 A | 1/1990 | Pawlak |
| 4,902,131 A | 2/1990 | Yamazaki et al. |
| 4,904,088 A | 2/1990 | Blazek et al. |
| 4,910,398 A | 3/1990 | Komatsu et al. |
| 4,912,034 A | 3/1990 | Kalra et al. |
| 4,927,266 A | 5/1990 | Sugiura et al. |
| 5,015,098 A | 5/1991 | Berg et al. |
| 5,020,169 A | 6/1991 | Hamada et al. |
| 5,068,909 A | 11/1991 | Rutherford et al. |
| 5,070,455 A | 12/1991 | Singer et al. |
| 5,097,119 A | 3/1992 | Breitmeier |
| 5,115,673 A | 5/1992 | Kline et al. |
| 5,126,577 A | 6/1992 | Trent |
| 5,134,662 A | 7/1992 | Bacus et al. |
| 5,244,787 A | 9/1993 | Key et al. |
| 5,254,845 A | 10/1993 | Burgess et al. |
| 5,309,108 A | 5/1994 | Maeda et al. |
| 5,422,018 A | 6/1995 | Saunders et al. |
| 5,427,910 A | 6/1995 | Kamentsky et al. |
| 5,432,054 A | 7/1995 | Saunders et al. |
| 5,439,649 A | 8/1995 | Tseung et al. |
| 5,489,386 A | 2/1996 | Saunders |
| 5,492,837 A | 2/1996 | Naser-Kolahzadeh et al. |
| 5,517,193 A | 5/1996 | Allison et al. |
| 5,523,207 A | 6/1996 | Kamentsky et al. |
| 5,561,556 A | 10/1996 | Weissman |
| 5,578,452 A | 11/1996 | Shi et al. |
| 5,587,833 A | 12/1996 | Kamentsky |
| 5,602,674 A | 2/1997 | Weissman et al. |
| 5,633,945 A | 5/1997 | Kamentsky |
| 5,672,881 A | 9/1997 | Striepeke et al. |
| 5,682,567 A | 10/1997 | Spruck et al. |
| 5,694,212 A | 12/1997 | Weissman |
| 5,717,198 A | 2/1998 | Broude et al. |
| 5,731,156 A | 3/1998 | Golbus |
| 5,784,529 A | 7/1998 | Richmond |
| 5,880,473 A | 3/1999 | Ginestet |
| 5,885,840 A | 3/1999 | Kamentsky et al. |
| 5,889,881 A | 3/1999 | MacAulay et al. |
| 5,916,750 A | 6/1999 | Iyer et al. |
| 5,948,359 A | 9/1999 | Kalra et al. |
| 5,962,234 A | 10/1999 | Golbus |
| 5,978,497 A | 11/1999 | Lee et al. |
| 6,002,788 A | 12/1999 | Luther |
| 6,026,174 A | 2/2000 | Palcic et al. |
| 6,031,930 A | 2/2000 | Bacus et al. |
| 6,049,220 A | 4/2000 | Borden et al. |
| 6,052,190 A | 4/2000 | Sekowski et al. |
| 6,087,134 A | 7/2000 | Saunders |
| 6,101,265 A | 8/2000 | Bacus et al. |
| 6,130,323 A | 10/2000 | Su et al. |
| 6,134,354 A | 10/2000 | Lee et al. |
| 6,137,899 A | 10/2000 | Lee et al. |
| 6,151,405 A | 11/2000 | Douglass et al. |
| 6,165,739 A | 12/2000 | Clatch |
| 6,169,816 B1 | 1/2001 | Ravkin |
| 6,215,892 B1 | 4/2001 | Douglass et al. |
| 6,221,607 B1 | 4/2001 | Tsipouras et al. |
| 6,225,636 B1 | 5/2001 | Ginestet |
| 6,226,392 B1 | 5/2001 | Bacus et al. |
| 6,239,868 B1 | 5/2001 | Jung et al. |
| 6,252,242 B1 | 6/2001 | Brunfeld et al. |
| 6,259,807 B1 | 7/2001 | Ravkin |
| 6,270,971 B1 | 8/2001 | Ferguson-Smith et al. |
| 6,272,235 B1 | 8/2001 | Bacus et al. |
| 6,292,582 B1 | 9/2001 | Lin et al. |
| 6,309,601 B1 | 10/2001 | Juncosa et al. |
| 6,330,349 B1 | 12/2001 | Hays et al. |
| 6,396,941 B1 | 5/2002 | Bacus et al. |
| 6,404,906 B2 | 6/2002 | Bacus et al. |
| 6,404,916 B1 | 6/2002 | De La Torre-Bueno |
| 6,408,048 B2 | 6/2002 | Opsal et al. |
| 6,418,236 B1 | 7/2002 | Ellis et al. |
| 6,445,817 B1 | 9/2002 | De La Torre-Bueno |
| 6,451,551 B1 | 9/2002 | Zhan et al. |
| 6,458,585 B1 | 10/2002 | Vachula et al. |
| 6,466,690 B2 | 10/2002 | Bacus et al. |
| 6,493,460 B1 | 12/2002 | MacAulay et al. |
| 6,495,106 B1 | 12/2002 | Kalra et al. |
| 6,518,554 B1 | 2/2003 | Zhang |
| 6,522,744 B1 | 2/2003 | Chiang |
| 6,524,798 B1 | 2/2003 | Goldbard et al. |
| 6,546,123 B1 | 4/2003 | McLaren et al. |
| 6,553,135 B1 | 4/2003 | Douglass et al. |
| 6,589,792 B1 | 7/2003 | Malachowski |
| 6,631,203 B2 | 10/2003 | Ellis et al. |
| 6,632,598 B1 | 10/2003 | Zhang et al. |
| 6,633,662 B2 | 10/2003 | Ravkin |
| 6,648,506 B2 | 11/2003 | McGrath et al. |
| 6,671,393 B2 | 12/2003 | Hays et al. |
| 6,674,058 B1 | 1/2004 | Miller |
| 6,674,896 B1 | 1/2004 | Torre-Bueno |
| 6,697,509 B2 | 2/2004 | De La Torre-Bueno |
| 6,718,053 B1 | 4/2004 | Ellis et al. |
| 6,746,873 B1 | 6/2004 | Buchanan et al. |
| 6,777,194 B1 | 8/2004 | Gerdes et al. |
| 6,778,714 B1 | 8/2004 | Kipman et al. |
| 6,780,377 B2 | 8/2004 | Hall et al. |
| 6,800,249 B2 | 10/2004 | De La Torre-Bueno |
| 6,816,625 B2 | 11/2004 | Lewis et al. |
| 6,852,986 B1 | 2/2005 | Lee et al. |
| 6,876,760 B1 | 4/2005 | Vaisberg et al. |
| 6,881,580 B1 | 4/2005 | Hall et al. |
| 6,882,873 B2 | 4/2005 | Samuels et al. |
| 6,900,426 B2 | 5/2005 | Zhang |
| 6,920,239 B2 | 7/2005 | Douglass et al. |
| 6,947,583 B2 | 9/2005 | Ellis et al. |
| 7,006,680 B2 | 2/2006 | Gulati |
| 7,024,316 B1 | 4/2006 | Ellison et al. |
| 7,064,829 B2 | 6/2006 | Li et al. |
| 7,070,951 B2 | 7/2006 | Zhang et al. |
| 7,084,386 B2 | 8/2006 | Bernardini et al. |
| 7,113,205 B2 | 9/2006 | Cappellaro |
| 7,116,354 B2 | 10/2006 | Rice et al. |
| 7,123,756 B2 | 10/2006 | Hakamata et al. |
| 7,129,053 B1 | 10/2006 | Reiter et al. |
| 7,133,543 B2 | 11/2006 | Verwoerd et al. |
| 7,133,545 B2 | 11/2006 | Douglass et al. |
| 7,146,062 B2 | 12/2006 | De La Torre-Bueno et al. |
| 7,171,054 B2 | 1/2007 | Fiete et al. |
| 7,173,663 B2 | 2/2007 | Skow et al. |
| 7,177,454 B2 | 2/2007 | McLaren et al. |
| 7,189,576 B2 | 3/2007 | Fukuoka et al. |
| 7,190,818 B2 | 3/2007 | Ellis et al. |
| 7,199,360 B1 | 4/2007 | Montagu |
| 7,205,154 B2 | 4/2007 | Corson |
| 7,212,660 B2 | 5/2007 | Wetzel et |
| 7,219,016 B2 | 5/2007 | Rimm et al. |
| 7,224,470 B2 | 5/2007 | Vaux et al. |
| 7,224,839 B2 | 5/2007 | Zeineh |
| 7,229,774 B2 | 6/2007 | Chinnaiyan et al. |
| 7,233,340 B2 | 6/2007 | Hughes et al. |
| 7,236,623 B2 | 6/2007 | Chapoulaud et al. |
| 7,257,267 B2 | 8/2007 | Recht |
| 7,269,280 B2 | 9/2007 | Hiroi et al. |
| 7,272,252 B2 | 9/2007 | De La Torre-Bueno et al. |
| 7,292,275 B2 | 11/2007 | Masuyama |
| 7,316,907 B2 | 1/2008 | Yu et al. |
| 7,330,250 B2 | 2/2008 | Gip et al. |
| 7,332,290 B2 | 2/2008 | Rubin et al. |
| 7,369,696 B2 | 5/2008 | Arini et al. |
| 7,376,256 B2 | 5/2008 | Kirsch et al. |
| 7,383,134 B2 | 6/2008 | Piper et al. |
| 7,440,637 B2 | 10/2008 | Schechner et al. |
| 7,474,777 B2 | 1/2009 | Kirsch et al. |
| 7,474,847 B2 | 1/2009 | Nikkanen et al. |
| 7,557,963 B2 | 7/2009 | Bhattacharjya |
| 7,639,350 B2 | 12/2009 | Noguchi et al. |
| 7,666,663 B2 | 2/2010 | Sugiyama et al. |
| 7,709,222 B2 | 5/2010 | Rimm et al. |
| 7,714,301 B2 | 5/2010 | Jackson et al. |
| 7,760,927 B2 | 7/2010 | Gholap et al. |

(56) References Cited

U.S. PATENT DOCUMENTS

| | | | |
|---|---|---|---|
| 7,767,393 B2 | 8/2010 | Chinnaiyan et al. | |
| 7,826,648 B2 | 11/2010 | Arai | |
| 7,847,239 B2 | 12/2010 | Lu et al. | |
| 7,873,215 B2 | 1/2011 | Xiao et al. | |
| 7,899,623 B2 | 3/2011 | Marcelpoil et al. | |
| 7,907,271 B2 | 3/2011 | Christiansen et al. | |
| 7,941,275 B2 | 5/2011 | Gholap et al. | |
| 8,160,348 B2 | 4/2012 | Pinard et al. | |
| 2003/0138827 A1 | 7/2003 | Kononen et al. | |
| 2003/0215936 A1 | 11/2003 | Kallioniemi et al. | |
| 2004/0014165 A1 | 1/2004 | Keidar et al. | |
| 2004/0027618 A1 | 2/2004 | Nakamura et al. | |
| 2004/0056966 A1 | 3/2004 | Schechner et al. | |
| 2004/0215087 A1 | 10/2004 | Genero et al. | |
| 2005/0037406 A1 | 2/2005 | De La Torre-Bueno et al. | |
| 2005/0105787 A1 | 5/2005 | Gulati | |
| 2005/0106712 A1* | 5/2005 | Chari et al. | 435/287.2 |
| 2005/0136509 A1 | 6/2005 | Gholap et al. | |
| 2005/0142579 A1 | 6/2005 | Sugiyama et al. | |
| 2005/0196040 A1 | 9/2005 | Ohara | |
| 2005/0266395 A1 | 12/2005 | Gholap et al. | |
| 2005/0282179 A1* | 12/2005 | Martin et al. | 435/6 |
| 2006/0001765 A1 | 1/2006 | Suda | |
| 2006/0015262 A1 | 1/2006 | Gholap et al. | |
| 2006/0063190 A1 | 3/2006 | Fischer et al. | |
| 2006/0127946 A1 | 6/2006 | Montagu et al. | |
| 2006/0160169 A1 | 7/2006 | Marcotte et al. | |
| 2006/0166253 A1 | 7/2006 | Kononen et al. | |
| 2006/0239533 A1 | 10/2006 | Tafas et al. | |
| 2006/0275844 A1 | 12/2006 | Linke et al. | |
| 2007/0114388 A1 | 5/2007 | Ogawa et al. | |
| 2007/0154958 A1 | 7/2007 | Hamann et al. | |
| 2007/0207489 A1 | 9/2007 | Pestano et al. | |
| 2008/0013816 A1 | 1/2008 | Rimm et al. | |
| 2008/0118437 A1 | 5/2008 | Pienta et al. | |
| 2008/0153098 A1 | 6/2008 | Rimm et al. | |
| 2008/0153877 A1 | 6/2008 | Adimoolam et al. | |
| 2009/0034823 A1 | 2/2009 | Christiansen et al. | |
| 2009/0074266 A1 | 3/2009 | Pinard et al. | |
| 2009/0074282 A1 | 3/2009 | Pinard et al. | |
| 2009/0086046 A1 | 4/2009 | Reilly et al. | |
| 2009/0167850 A1 | 7/2009 | Bruno et al. | |
| 2011/0116086 A1 | 5/2011 | Christiansen et al. | |
| 2011/0116087 A1 | 5/2011 | Christiansen et al. | |
| 2011/0228993 A1 | 9/2011 | Reilly et al. | |

FOREIGN PATENT DOCUMENTS

| | | |
|---|---|---|
| EP | 0 977 981 A1 | 2/2000 |
| EP | 0 720 114 | 1/2001 |
| EP | 1 065 496 | 3/2001 |
| EP | 1 202 563 | 5/2002 |
| EP | 1 251 179 | 10/2002 |
| EP | 1 300 713 | 4/2003 |
| EP | 1 329 513 | 7/2003 |
| EP | 1 347 285 A1 | 9/2003 |
| EP | 1 779 088 | 2/2006 |
| EP | 1 502 098 | 9/2008 |
| GB | 2 305 723 | 4/1997 |
| GB | 2 395 263 | 5/2004 |
| GB | 2 396 406 | 6/2004 |
| GB | 2 406 908 | 4/2005 |
| GB | 2 423 150 | 8/2006 |
| GB | 2 430 026 | 3/2007 |
| JP | 02-232550 A | 9/1990 |
| JP | 04-315119 A | 11/1992 |
| JP | 05-249102 A | 9/1993 |
| JP | 07-030753 | 1/1995 |
| JP | 11-183381 A | 7/1999 |
| JP | 2001-211896 A | 8/2001 |
| JP | 2003-284713 A | 10/2003 |
| JP | 2003-294734 A | 10/2003 |
| JP | 2004-157018 A | 6/2004 |
| JP | 2004-219513 A | 8/2004 |
| JP | 2004-354346 A | 12/2004 |
| JP | 2005-070537 A | 3/2005 |
| JP | 2006-194711 A | 7/2006 |
| JP | 2007-127485 A | 5/2007 |
| JP | 2007-232631 A | 9/2007 |
| JP | 2007-271484 A | 10/2007 |
| JP | 2007-278984 A | 10/2007 |
| WO | WO-95/34050 | 12/1995 |
| WO | WO-96/09604 | 3/1996 |
| WO | WO-96/09605 | 3/1996 |
| WO | WO-96/23898 | 8/1996 |
| WO | WO-98/07022 | 2/1998 |
| WO | WO-99/30278 | 6/1999 |
| WO | WO-00/64147 | 10/2000 |
| WO | WO-00/79326 A1 | 12/2000 |
| WO | WO-02/056584 | 7/2002 |
| WO | WO-02/067188 | 8/2002 |
| WO | WO-02/086498 | 10/2002 |
| WO | WO-02/099429 | 12/2002 |
| WO | WO-03/008963 | 1/2003 |
| WO | WO-03/056343 | 7/2003 |
| WO | WO-03/093810 | 11/2003 |
| WO | WO-03/097850 | 11/2003 |
| WO | WO-03/098522 | 11/2003 |
| WO | WO-2004/017052 A2 | 2/2004 |
| WO | WO-2004/025569 | 3/2004 |
| WO | WO-2004/059288 | 7/2004 |
| WO | WO-2005/027015 | 3/2005 |
| WO | WO-2005/033706 | 4/2005 |
| WO | WO-2005/045734 | 5/2005 |
| WO | WO-2005/076197 | 8/2005 |
| WO | WO-2005/076216 | 8/2005 |
| WO | WO-2005/077263 | 8/2005 |
| WO | WO-2005/096225 | 10/2005 |
| WO | WO-2005/114578 | 12/2005 |
| WO | WO-2006/036726 | 4/2006 |
| WO | WO-2006/036788 | 4/2006 |
| WO | WO-2006/039396 | 4/2006 |
| WO | WO-2006/054991 | 5/2006 |
| WO | WO-2006/083969 A2 | 8/2006 |
| WO | WO-2006/102233 | 9/2006 |
| WO | WO-2006/105519 | 10/2006 |
| WO | WO-2006/122251 | 11/2006 |
| WO | WO-2006/133325 A2 | 12/2006 |
| WO | WO-2007/024264 | 3/2007 |
| WO | WO-2007/133465 | 11/2007 |
| WO | WO-2008/012771 | 1/2008 |
| WO | WO-2008/143849 A2 | 11/2008 |
| WO | WO 2008/143849 A2 * | 11/2008 |
| WO | WO-2008/156669 A1 | 12/2008 |
| WO | WO-2009/020621 A1 | 2/2009 |
| WO | WO-2009/020972 A2 | 2/2009 |
| WO | WO-2009/029810 A1 | 3/2009 |
| WO | WO-2010/033508 A1 | 3/2010 |

OTHER PUBLICATIONS

Schweitzer et al. Multiplexed protein profiling on microarrays by rolling-circle amplification. Nature Biotechnology, vol. 20, 2002, pp. 359-365.*

Christiansen et al. Quantitative proteomics using AQUA™ technology. Human Immunology, Oct. 2006, vol. 67, p. S43.*

Bibliographic data for [Christiansen et al. Quantitative proteomics using AQUA™ technology. Human Immunology, Oct. 2006, vol. 67, p. S43] obtained online on Sep. 10, 2014 from <<http://search.proquest.com>> 2 pages.*

Camp et al. Automated subcellular localization and quantification of protein expression in tissue microarrays. Nature Medicine, vol. 8, 2002, pp. 1323-1328.*

Machine learning. Websters new world computer dictionary, 2003, 2 pages. Hoboken, NJ: Wiley. Retrieved online from <http://www.credoreference.com>> on Mar. 12, 2015.*

A.K. Jain et al, "Data Clustering: A Review", ACM Computing Surveys, vol. 31, No. 3, Sep. 1999, pp. 264-323.

A.K. Katoh et al., "Immunoperoxidase Staining for Estrogen and Progesterone Receptors in Archival Formalin Fixed, Paraffin Embedded Breast Carcinomas after Microwave Antigen Retrieval," Biotechnic & Histochemistry, vol. 72, No. 6, pp. 291-298, Nov. 1997.

(56) References Cited

OTHER PUBLICATIONS

A.R. Leitch, In Situ Hybridization: A Practical Guide, Oxford BIOS Scientific Publishers, Microscopy Handbooks (1994), contents only.

Aaron J. Berger et al., "Automated Quantitative Analysis of HDM2 Expression in Malignant Melanoma Shows Associaion with Early-Stage Disease and Improved Outcome," Cancer Research, vol. 64, Dec. 2004, pp. 8767-8772.

Anthony McCabe, M. Dolled-Filhart, R. L. Camp, D. L. Rimm, "Automated Quantitative Analysis (AQUA) of In Situ Protein Expression, Antibody Concentration, and Prognosis," Journal of the National Cancer Institute, vol. 97, No. 24, Dec. 21, 2005.

Chen, et al., "Ratio-Based Decisions and the Quantitative Analysis of cDNA Microarray Images," Journal of Biomedical Optics, SPIE, Bellingham, WA, vol. 2, No. 4, Oct. 1, 1997, pp. 364-374.

Communication mailed Apr. 28, 2010 in European Appln No. 08754418.5.

D.R.J. Snead et al., "Methodology of Immunohistological Detection of Oestrogen Receptor in Human Breast Carcinoma in Formalin-Fixed, Paraffin-Embedded Tissue: A Comparison with Frozen Section Methodology," Histopathology, vol. 23, pp. 233-238, 1993.

David J. Miller et al., "Emergent Unsupervised Clustering Paradigms with Potential Application to Bioinformatics," Frontiers in Bioscience, vol. 13, Jan. 2008, pp. 677-690.

David L. Rimm, MD PhD., et al., "Tissue Microarray: A New Technology for Amplification of Tissue Resources," The Cancer Journal, vol. 7, No. 1, Jan./Feb. 2001, pp. 24-31.

Duggan, et al., "Expression Profiling Using cDNA Microarrays," Nature Genetics, Nature Publishing Group, New York, vol. 21, No. Suppl., Jan. 1, 1999, pp. 10-14.

Feng, et al., "Adaptive Kurtosis Optimization Autofocus Algorithm," Journal of Electronics, vol. 23, No. 4, Jul. 2006, pp. 532-534.

Gina G. Chung et al., "Tissue Microarray Analysis of B-Catenin in Colorectal Cancer Shows Nuclear Phospho-B-catenin Is Associated with a Better Prognosis," Clinical Cancer Research, vol. 7, pp. 4013-2010, Dec. 2001.

J. Sambrook, E. F. Fritsch, and T. Maniatis. (1989) Molecular cloning, a laboratory manual. Cold Spring Harbor Laboratory Press, Cold Spring Harbor, N.Y., 30 pages.

Jacqueline F. McGinty et al., "Double Immunostaining Reveals Distinctions Among Opioid Peptidergic Neurons in the Medical Basal Hypothalamus," Brain Research, vol. 278, pp. 145-153, 1983, Elsevier.

Jules M. Elias, PhD., Immunoshistopathology A Practical Approach to Diagnosis,: American Society of Clinical Pathologists, Chicago, 1990, contents only.

Kononen, Juha et al., "Tissue Microarrays for High-Throughput Molecular Profiling of Tumor Specimens," Nature Medicine, vol. 4, No. 7, Jul. 1998, pp. 844-847.

M. Cregger et al., "Immunohistochemistry and Quantative Analysis of Protein Expression," Arch Pathol Lab Med, vol. 130, Jul. 2006, pp. 1026-1030.

Marisa Dolled-Filhart et al., "Classification of Breast Cancer Using Genetic Algorithms and Tissue Microarryas," Clin Cancer Research, vol. 12(21), pp. 6459-6468, Nov. 1, 2006, www.aacrjournals.org.

Marisa Dolled-Filhart et al., "Tissue Microarray Analysis of Signal Transducers and Activators of Transcription 3 (Stat3) and Phospho-Stat3 (Tyr705) in Node-negative Breast Cancer Shows Nuclear Localization Is Associated with a Better Prognosis," Clinical Cancer Research, vol. 9, Feb. 2003, pp. 594-600.

Molecular Devices, Corp., "GenePix Pro 6.0 Microarray Acquisition and Analysis Software for GenePix Microarray Scanners—User's Guide and Tutorial," GenePix Pro 6.0—Molecular Devices, Corp., Feb. 2005.

Notice of Allowance mailed Dec. 8, 2010 in U.S. Appl. No. 12/139,370.

Notice of Allowance mailed May 6, 2011 in U.S. Appl. No. 13/012,707.

Office Action mailed Apr. 14, 2011 in U.S. Appl. No. 13/010,643.

Office Action mailed May 12, 2010 in U.S. Appl. No. 12/139,370.

Olli-P. Kallioniemi et al., "Tissue Microarray Technology for High-Throughput Molecular Profiling of Cancer," Human Molecular Genetics, vol. 10, No. 7, 2001, pp. 657-662.

Robert L. Camp et al., "Quantitative Analysis of Breast Cancer Tissue Microarrays Shows That Both High and Normal Levels of HER2 Expression are Associated with Poor Outcome," Cancer Research, vol. 63, Apr. 2003, pp. 1445-1448.

Robert L. Camp et al., "Automated Subcellular Localization and Quantification of Protein Expression in Tissue Microarrays," New Technology—Nature Medicine, 2002, vol. 8, No. 11, pp. 1323-1327.

Search Report mailed Feb. 17, 2009 in International Appln No. PCT/US2008/006116.

Search Report mailed Jun. 12, 2009 in International Appln No. PCT/US2008/072235.

Search Report mailed Nov. 13, 2008 in International Appln No. PCT/US2008/074817.

Search Report mailed Nov. 18, 2008 in International Appln. No. PCT/US2008/09454.

Search Report mailed Nov. 24, 2008 in International Appln. No. PCT/US2008/007399.

Trevor Jowett, "Tissue In Situ Hybridization: Methods in Animal Development," John Wiley & Sons, Inc. and Spektrum Akademischer Verlag, 1997.

International Search Report and Written Opinion mailed Jan. 25, 2010 in corresponding International Application No. PCT/US2009/056996, 11 pgs.

Dell' Anna , R. et al., "An Automated Procedure to Properly Handle Digital Images in Large Scale Tissue Micorarray Experiments", Computer Methods and Programs in Biomedicine, vol. 79, No. 3, Sep. 1, 2005, pp. 197-208.

Gustavson , Mark D. et al, "Development of an Unsupervised Pixel-based Clustering Algorithm for Compartmentalization of Immunohistochemical Expression Using Automated Quantitative Analysis", Applied Immunohistochemistry, vol. 17, No. 4, Jul. 2009, pp. 329-337.

Jain, Anil K., "Fundamentals of Digital Image Processing", Image Analysis and Computer Vision, Chapter 9, Jan. 1, 1989, p. 418, XP-002562566.

Teverovskiy, Mikhail et al., "Automated Localization and Quantification of Protein Multiplexes via Multispectral Fluorescence Imaging", Biomedical Imaging: From Nano to Macro, 2008, ISBI 2008, 5th IEEE International Symposium on, IEEE, May 14, 2008, pp. 300-303.

Butler "Enzyme-Linked Immunosorbent Assay," Journal of Immunoassay, vol. 21(2&3), 2000, pp. 165-209.

Camp et al., "X-Tile: A New Bio-Informatics Tool for Biomarker Assessment and Outcome-Based Cut-Point Optimization," Clinical Cancer Research, vol. 10, 2004, pp. 7252-7259.

Demir et al, "Automated cancer diagnosis based on histopathological images: a systematic survey," Rensselaer Polytechnic Institute, Department of Computer Science, Technical Report TR-05-09, Published 2005.

Dolled-Filhart et al., "Quantitive In Situ Analysis of B-Catenin Expression in Breast Cancer Shows Decreased Expression is Associated with Poor Outcome," Cancer Res., vol. 66, No. 10, 2006, pp. 5487-5494.

Giltnane et al., Technology Insight: "Identification of Biomarkers With Tissue Microarray Technology," Nature Clinical Practice Oncology, vol. 1, No. 2. (Dec. 2004), pp. 104-111.

Harvey et al., "Estrogen Receptor Status by Immunohistochemistry is Superior to the Ligand-Binding Assay for Predicting Response to Adjuvant Endocrine Therapy in Breast Cancer," Journal of Clinical Oncology, vol. 17, No. 5, 1999, pp. 1474-1481.

Lillie, "H.J. Conn's Biological Stains: A Handbook on the Nature and Uses of the Dyes Employed in the Biological Laboratory," The Williams & Wilkins Company, copyright 1969, Eighth Edition.

Office Action—Communication pursuant to Article 94(3) EPC—for EP 08768439.5—dated Oct. 12, 2012.

Office Action mailed Aug. 7, 2012 in Japan Application No. 2010-508400, with translation, 7 pgs.

Paik et al., "Benefit from Adjuvant Trastuzumab May Not Be Confined to Patients With IHC 3 and/or FISH Positive Tumors: Central Testing Results from NSABP B-31," vol. 25, 2007, pp. 511.

(56) References Cited

OTHER PUBLICATIONS

Perez et al., "HER2 Testing by Local, Central, and Reference Laboratories in Specimens from the North Central Cancer Treatment Group N9831 Intergroup Adjuvant Trial", Journal of Clinical Oncology, vol. 24, 2006, pp. 3032-3038.

Raeside, et al., "Monte Carlo Principles and Application," Phs Med Biol., vol. 21, No. 2, 1976, pp. 181-197.

Roth, et al., "Enzyme-based Antigen Localization and Quantitation in Cell and Tissue Samples (Midwestern Assay)," The Journal of Histochemistry & Cytochemistry, vol. 45(12), pp. 1629-1641, 1997.

Wiemann, et al., Coley's Toxins, Tumor Necrosis Factor and Cancer Research: A Historical Perspective; Pharmacol. Ther., 64:529-564 (1994), abstract only.

Wolff, et al., Arch Pathol Lab Med., "American Society of Clinical Oncology/College of American Pathologists Guideline Recommendations for Human Epidermal Growth Factor Receptor 2 Testing in Breast Cancer," vol. 131, Jan. 2007, p. 18-43.

Office Action for EP Application No. 08768439.5 dated Oct. 31, 2014.

Office Action in EP Application No. 09792559.8 dated Oct. 27, 2014.

Office Action Reasons for Rejection in Japanese Patent Application No. 2010-512196 dated Jan. 21, 2014.

Notice of Allowance on U.S. Appl. No. 13/867,817 dated Nov. 6, 2014.

US Office Action on U.S. Appl. No. 13/867,817 dated Jun. 30, 2014.

Invitation pursuant to Article 94(3) and Rule 71(1) EPC issued in European Application No. 09 792 559.8 mailed Mar. 27, 2015.

Notice of Allowance issued in co-pending U.S. Appl. No. 13/867,817 mailed Mar. 18, 2015.

Office Action issued in co-pending Chinese Application No. 200980137750.0 mailed Mar. 11, 2015.

\* cited by examiner

|  | Instrument 1 (Reference) | | |
|---|---|---|---|
|  | POS | NEG | TOT |
| Instrument 2 POS | 87 | 9 | 96 |
| NEG | 4 | 483 | 487 |
| TOT | 91 | 492 | 583 |

Overall Concordance: 97.8%(95CI:96.3-98.6)
Positive Agreement: 95.6%(95CI:90.9-98.1)
Negative Agreement: 98.2%(95CI:97.3-98.6)

B.

|  | Instrument 1 (Reference) | | |
|---|---|---|---|
|  | POS | NEG | TOT |
| Instrument 3 POS | 71 | 12 | 83 |
| NEG | 20 | 480 | 500 |
| TOT | 91 | 492 | 583 |

Overall Concordance: 94.5%(95CI:92.5-96.0)
Positive Agreement: 78.0%(95CI:71.6-82.7)
Negative Agreement: 97.6%(95CI:96.4-98.4)

C.

|  | Operator 1 (Reference) | | |
|---|---|---|---|
|  | POS | NEG | TOT |
| Operator 2 POS | 71 | 1 | 72 |
| NEG | 3 | 508 | 511 |
| TOT | 74 | 509 | 583 |

Overall Concordance: 99.3%(95CI:98.3-99.6)
Positive Agreement: 95.9%(95CI:91.9-97.0)
Negative Agreement: 99.8%(95CI:99.2-100)

D.

|  | Operator 1 (Reference) | | |
|---|---|---|---|
|  | POS | NEG | TOT |
| Operator 3 POS | 73 | 10 | 83 |
| NEG | 1 | 499 | 500 |
| TOT | 74 | 509 | 583 |

Overall Concordance: 98.1%(95CI:96.9-98.4)
Positive Agreement: 98.6%(95CI:93.9-99.8)
Negative Agreement: 98.0%(95CI:97.3-98.2)

E.

|  | Run 1 (Reference) | | |
|---|---|---|---|
|  | POS | NEG | TOT |
| Run 2 POS | 52 | 1 | 53 |
| NEG | 20 | 510 | 530 |
| TOT | 72 | 511 | 583 |

Overall Concordance: 96.4%(95CI:95.1-96.7)
Positive Agreement: 72.2%(95CI:67.0-73.4)
Negative Agreement: 99.8%(95CI:99.1-100)

F.

|  | Run 1 (Reference) | | |
|---|---|---|---|
|  | POS | NEG | TOT |
| Run 3 POS | 60 | 18 | 78 |
| NEG | 12 | 493 | 505 |
| TOT | 72 | 511 | 583 |

Overall Concordance: 94.9%(95CI:92.9-96.3)
Positive Agreement: 83.3%(95CI:75.5-89.2)
Negative Agreement: 96.5%(95CI:95.4-97.3)

| AQUA® SCORE Comparison | Correlation | | Multinomial Regression | |
|---|---|---|---|---|
| | Spearman R | p-value | p-value | Pseudo $R^2$ |
| Pathologist 1 | 0.938 | <0.001 | <0.001 | 0.861 |
| Pathologist 2 | 0.940 | <0.001 | <0.001 | 0.866 |
| Pathologist 3 | 0.935 | <0.001 | <0.001 | 0.855 |

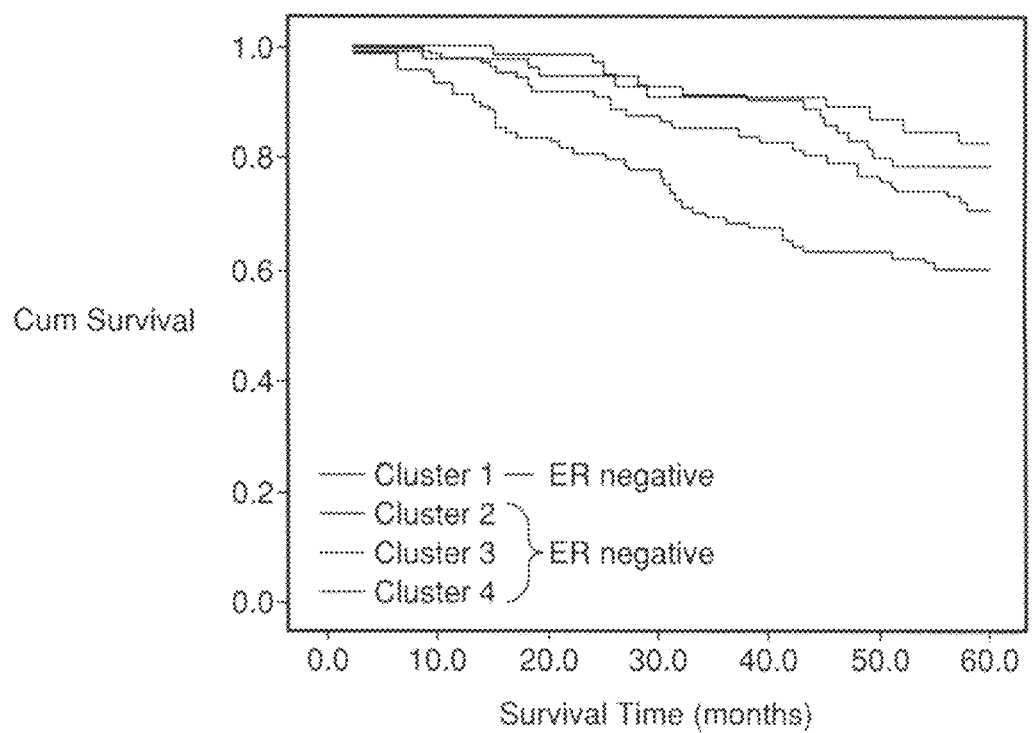

REPRODUCIBLE QUANTIFICATION OF BIOMARKER EXPRESSION

CROSS REFERENCE TO RELATED APPLICATIONS

The present application claims priority benefit under 35 U.S.C. §119(e) of U.S. Pat. Appl. No. 61/097,415, filed Sep. 16, 2008, the disclosure of which is hereby incorporated by reference in its entirety.

BACKGROUND OF THE INVENTION

The present invention relates to the field of automated biomarker expression analysis in tissue samples using algorithms to enhance operator-independent analysis and assay result reproducibility for greater predictive value in diagnostic assays.

To date, biomarker assessment on tissue sections relies on traditional cytochemical and immunohistochemical (IHC) techniques which were largely developed before large scale and high throughput assays were available. A significant drawback to traditional methods is the subjective nature of the test, and lack of standardization. Although IHC tests have shown clinical utility (e.g., Her2/HercepTest), the value of these tests have recently been shown to be compromised by the site at which the test is performed. Two recent studies examining the reproducibility of Her2 testing has shown that there may be as much as 20% error between local and central lab testing (Perez et al. J. Clinic. One. (2006) 24:3032-8; Paik S et al. Benefit from adjuvant trastuzumab may not be confined to patients with IHC 3+ and/or FISH positive tumors: Central testing results from NSABP B-31 (2007) 25:511-22).

Tissue microarray technology offers the opportunity for high throughput analysis of tissue samples (Konen, J. et al., Nat. Med. 4:844-7 (1998); Kallioniemi, O. P. et al., Hum. Mol. Genet. 10:657-62 (2001); Rimm, D. L. et al., Cancer J. 7:24-31 (2001)). For example, the ability to rapidly perform large scale studies using tissue microarrays can provide critical information for identifying and validating drug targets and prognostic markers (e.g. estrogen receptor (ER) and HER2/neu), as well as candidate therapeutics.

The present invention provides for the first time fully automated standardization of in situ biomarker quantification that minimizes lab-to-lab, machine-to-machine, operator-to-operator, and day-to-day staining variations.

SUMMARY OF THE INVENTION

The present invention relates to the reproducible quantification of biomarker expression from tissue samples, whole tissue sections (WTS) as well as tissue microarrays (TMAs), so as to reduce variability between runs or batches due to differences in operators, equipment, facilities, and other factors. The systems and processes described herein provide the automated localization and quantitation of biomarkers with normalization of scores for greater reproducibility between runs, regardless of location, operator or instrument variability.

One embodiment of the invention relates to a method of reproducibly quantifying biomarker expression in a slide-mounted tissue sample comprising (a) obtaining a slide-mounted tissue sample, which has been stained to permit localization of at least one cellular compartment and at least one biomarker, (b) obtaining one or more pixel-comprised images of the stained tissue sample using a standardized optical system that includes a light source, (c) automatically analyzing one or more data sets derived from the image pixels to differentiate data signal from noise, (d) automatically analyzing one or more data sets derived from the image pixels to differentiate data signal attributable to each of said at least one cellular compartment, (e) optionally automatically analyzing one or more data sets derived from the image pixels to differentiate data signal attributable to said at least one biomarker for each of said at least one cellular compartment, (f) quantifying the amount of biomarker expressed in each of said at least one cellular compartment; whereby the biomarker expression in the slide-mounted tissue sample is quantified reproducibly.

In one embodiment, the standardized optical system includes a light source whose intensity and optical path variability have been normalized. In a further embodiment, the standardized optical system allows for automatic adjustment of exposure time to provide an optimized dynamic range of data captured in the image pixels.

In one embodiment, each automatic analysis step is carried out in an unsupervised manner.

In one embodiment, the data signal attributable to two or more cellular compartments is differentiated.

In one embodiment, the amount of biomarker expressed in each of two or more cellular compartments is quantified.

In one embodiment, the data signal attributable to two or more cellular compartments is differentiated with a confidence interval of about 95%.

In one embodiment, the method further comprises assessing the quality of the one or more slide-mounted tissue samples or the one or more pixel-comprised images or one or more magnified portions thereof.

In one embodiment, the method provides a reproducible cutpoint determination.

In one embodiment, the method provides a greater than 85% concordance for sample classification from one run to another for each sample. In a further embodiment, the method provides a greater than 90% concordance for sample classification from one run to another for each sample.

In one embodiment, the method provides a quantified measure of biomarker expression having a level of reproducibility above 80 percent. In a further embodiment, the method provides a quantified measure of biomarker expression having a level of reproducibility above 90 percent. In a further embodiment, the method provides a quantified measure of biomarker protein expression having a level of reproducibility above 95 percent.

In one embodiment, the method provides a quantified measure of biomarker expression having a level of reproducibility falling in the range of about 90 to about 97 percent.

In one embodiment, the method provides a quantified measure of biomarker expression having a coefficient of variation (% CV) below 20 percent. In a further embodiment, the method provides a quantified measure of biomarker expression having a coefficient of variation (% CV) below 10 percent. In a further embodiment, the method provides a quantified measure of biomarker expression having a coefficient of variation (% CV) below 5 percent. In a further embodiment, the method provides a quantified measure of biomarker expression having a coefficient of variation (% CV) falling in the range of about 4 to about 7 percent.

In one embodiment, the slide-mounted tissue sample has been stained with an optimal dilution of one or more reagents. In a further embodiment, said optimal dilution produces one or more pixel-comprised images having an optimal dynamic range metric.

In one embodiment, the method of the present invention is implemented by a computer. In another embodiment, the present invention is directed to a computer readable medium comprising the computer readable instructions stored thereon for execution by a processor to perform the method described herein. In another embodiment, the present invention is directed to an electromagnetic signal carrying computer-readable instructions for implementing the method described herein. The invention is also directed to a computer readable medium having computer readable instructions stored thereon for execution by a processor to perform a method of reproducibly quantifying biomarker expression in a slide-mounted tissue sample comprising: (a) acquiring one or more pixel-comprised images of a slide-mounted tissue sample, which has been stained to permit localization of at least one cellular compartment and at least one biomarker using a standardized optical system that includes a light source; (b) automatically analyzing one or more data sets derived from the image pixels to differentiate data signal from noise; (c) automatically analyzing one or more data sets derived from the image pixels to differentiate data signal attributable to each of said at least one cellular compartment; and (d) quantifying the amount of biomarker expressed in each of said at least one cellular compartment, whereby the biomarker expression in the slide-mounted tissue sample is quantified reproducibly. In a preferred embodiment of the computer readable medium, the computer readable instructions stored thereon for execution by a processor further comprises instructions to perform a method that includes, prior to said quantifying step, an optional step of automatically analyzing one or more data sets derived from the image pixels to differentiate data signal attributable to said at least one biomarker for each of said at least one cellular compartment. In yet another embodiment of the invention, a system for reproducibly quantifying biomarker expression in a slide-mounted tissue sample comprising: (a) one or more lenses configured to magnify at least a portion of a slide-mounted tissue sample, which has been stained to permit localization of at least one cellular compartment and at least one biomarker; (b) a standardized optical system, including a light source and an image sensor in optical communication with said one or more lenses, the standardized optical system obtaining one or more pixel-comprised images of the stained tissue sample; (c) a processor module in communications with the standardized optical system, the processor module configured to: (i) automatically analyze one or more data sets derived from the image pixels to differentiate data signal from noise, (ii) automatically analyze one or more data sets derived from the image pixels to differentiate data signal attributable to each of said at least one cellular compartment, and (iii) quantify the amount of biomarker expressed in each of said at least one cellular compartment, whereby the biomarker expression in the slide-mounted tissue sample is quantified reproducibly. In a preferred embodiment of the system, the processor module is further configured to optionally automatically analyze one or more data sets derived from the image pixels to differentiate data signal attributable to said at least one biomarker for each of said at least one cellular compartment. Such analysis is preferably performed prior to the quantification step (iii).

Other features, objects and advantages of the invention will be apparent from the following figures, detailed description and the claims.

BRIEF DESCRIPTION OF THE DRAWINGS

FIGS. 6A-F show 2×2 contingency tables comparing positive (POS) v. negative (NEG) population segregation based on X-tile cut-points generated for the reference (e.g., Instrument 1) for each indicated instrument set (A, B), operator set (C, D), and run set (E, F). Also shown are overall concordance, positive agreement, and negative agreement rates with 95% confidence intervals.

FIGS. 9A-D show the results from Example 4, below. FIGS. 9A-C are box plots of the Allred score from three pathologists compared to the AQUA® score generated for the same samples. FIG. 9D is a table showing the correlation between the Allred and AQUA® scoring for each pathologist.

FIGS. 10A-B show the (A) clustering of patients based on AQUA® scores and (B) survival of the clustered groups, as described in Example 4.

DETAILED DESCRIPTION OF THE PREFERRED EMBODIMENTS

Unless defined otherwise, all technical and scientific terms used herein generally have the same meaning as commonly understood by one of ordinary skill in the art to which this invention belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell biology, immunohistochemistry, and imaging (e.g., cells and tissue) described below are those well known and commonly employed in the art.

It should be appreciated that the particular implementations shown and described herein are examples of the present invention and are not intended to otherwise limit the scope of the present invention in any way. Further, the techniques are suitable for applications in teleconferencing, robotics vision, unmanned vehicles, or any other similar applications.

Techniques suitable for use in the present invention can also be found in co-pending U.S. application Ser. Nos. 12/153,171, filed May 14, 2008; U.S. application Ser. No. 12/139,370, filed Jun. 13, 2008; U.S. application Ser. No. 12/186,294, filed Aug. 5, 2008; U.S. application Ser. No. 12/188,133, filed Aug. 7, 2008; and U.S. application Ser. No. 12/201,753, filed Aug. 29, 2008, each of which is hereby incorporated by reference in its entirety.

Figure 1:
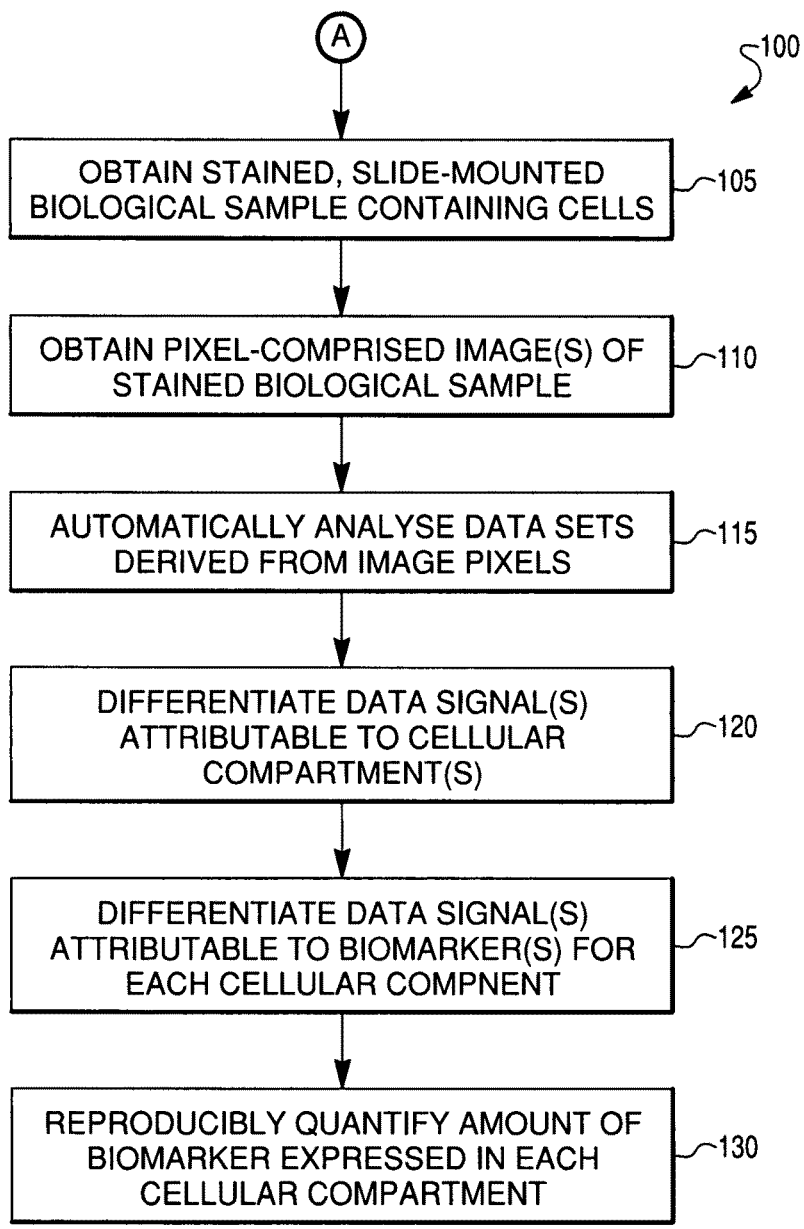
FIG. 1 shows an embodiment of a process for reproducibly quantifying an amount of a biomarker expressed in each of one or more cellular components of a slide-mounted biological sample containing cells, such as a tissue sample from a patient.

FIG. 1 shows a process for reproducibly quantifying an amount of a biomarker expressed in each of one or more cellular components of a slide-mounted biological sample containing cells, such as a tissue sample from a patient. The process 100 is initiated by obtaining a stained, slide-mounted biological sample containing cells 105, in which the stain has been applied in a manner to permit localization of at least one cellular compartment and at least one biomarker. The at least one cellular compartment includes, but is not limited to, a cytoplasm, a nucleus, and a cell wall. The at least one biomarker may include a biomarker labeled or detected via a CY5 fluorescent signal, used to detect a tumor cell. Examples include but are not limited to HER2, ER, PR, EGFR, ERCC1, TS and the like.

The process 100 continues by obtaining a pixel-comprised image or set of images of the stained tissue sample 110. The pixel-comprised image or set of images may be taken using a standardized optical system, such as an optical microscope system, that includes a light source. The pixel-comprised image may be obtained through the standardized optical system using a digital image sensor, such as a digital camera. In some embodiments, the digital image may be taken by an analogue camera, whereby the resulting analogue image or film is digitized by a digital scanner or equivalent means. In at least some embodiments, the camera may be mounted directly or indirectly to a microscope to obtain a pixel-comprised image in the form of a micrograph. Alternately or in addition to, the camera may rely on a direct connection to a video out line on an existing imaging system. In some embodiments, the light source includes light with wavelengths in one or more of the visible spectrum, the infrared (IR) spectrum, and the ultraviolet (UV) spectrum. The camera may be a video camera or a time-lapse photographic sequence, providing real-time and elapsed time images that contain dynamic cellular activity.

The pixel-comprised image obtained by the process 100 is then analyzed to derive one or more data sets from the image pixels to differentiate a data signal from noise 115. This analysis can be performed automatically, for example, using a processor. The processor may include one or more computer processors, controllable according to a preprogrammed instruction set. In some embodiments differentiating a data signal from noise includes a statistical analysis of the signal, for example an unsupervised cluster analysis resulting in segregation of pixels with signal from pixels having signal attributable to noise. In some embodiments, differentiating a data signal from noise may include subtracting a focused image of the slide-mounted tissue sample from a defocused image of the slide-mounted tissue sample. In some embodiments, the defocused image may include an image focused just below the slide-mounted tissue sample. In general, defocusing an image acts like a spatial low pass filter, allowing for a background measurement to which the data signal may be compared.

Next, the pixel-comprised image obtained by the process 100 is analyzed to derive one or more data sets from the image pixels to differentiate data signals attributable to each of at least one cellular compartment 120. This analysis can also be performed automatically, for example, using a preprogrammed computer or a dedicated special purpose processor. In some embodiments, differentiation may depend on a fluorescence attributable to a marker or stain applied to the slide-mounted sample. In some embodiments, the fluorescence of stains directed to the at least one cellular compartment varies in wavelength. In some embodiments, a blue fluorescence may be associated with a nucleus receptor (DAPI), a green fluorescence may be associated with a cell cytoplasm receptor (cytokeratin), and a red fluorescence may be associated with a cell membrane receptor (alpha-catenin).

Preferably, the stain is applied in a manner to permit localization of at least one cellular compartment and at least one biomarker. In some embodiments, the at least one biomarker, previously described in 105, is used to detect a tumor cell or a target protein or a target antigen and may be an indication of a tumor cell in the slide-mounted tissue sample. The process 100 includes a step to associate or otherwise to correlate the previously differentiated data signals attributable to each of at least one cellular compartments 120 with the detected tumor cell or tumor mask. In doing so, the one or more data sets derived from the image pixels are automatically analyzed to differentiate a data signal attributable to at least one biomarker for each of the at least one cellular compartment 125. The process 100 reproducibly quantifies the amount of biomarker expressed in at least one of the at least one cellular compartment for the slide-mounted tissue sample 130.

Figure 2:
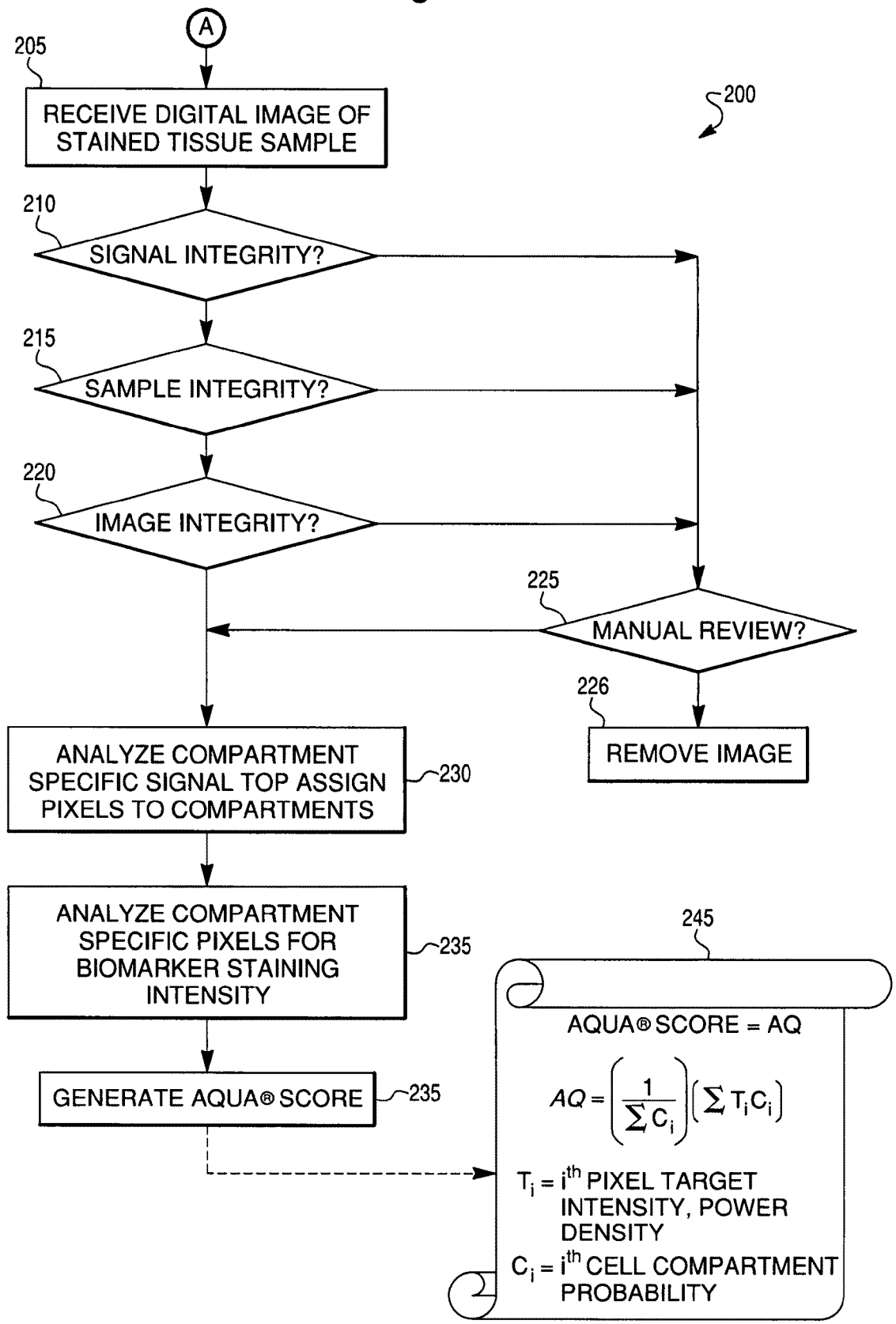
FIG. 2 shows an embodiment of a process for image processing steps to reproducibly quantifying an amount of a biomarker expressed in each of one or more cellular components of a slide-mounted biological sample containing cells.

FIG. 2 shows a detailed process 200 for image processing steps to reproducibly quantifying an amount of a biomarker expressed in each of one or more cellular components of a slide-mounted sample. The process 200 is initiated by obtaining a digital image of a stained tissue sample 205. The digital image is obtained in a manner similar to that described in steps 105, 110 in method 100. Next, the process 200 directs the image quality to be tested for signal integrity 210, sample integrity 215, and image integrity 220. If any one or more image quality tests of signal integrity 210, sample integrity 215, and image integrity 220 fail, the digital image may be removed from analysis or may be flagged for a manual review of the digital image by the operator 225 to either accept the digital image for analysis or to remove the digital image from analysis 226.

Passing image quality tests for signal integrity 210, sample integrity 215, and image integrity 220 or passing a manual review of the digital image 225 identifies the digital image as a candidate for further image processing in process 200. Failure to pass image quality tests for any one or more of signal integrity 210, sample integrity 215, and image integrity 220 and failing to pass a manual review of the digital image 225 identifies the digital image as low quality, and the digital image is rejected. Briefly, signal integrity includes a cellular compartmentalization, a fluorescence intensity, and a saturated pixel percentage assessment. Saturation may be assessed by determining that a predetermined number of pixels in the pixel-comprised image are represented by data and data structures that include a maximum or near maximum value. Sample integrity includes a determination that a sufficient sample of interest (e.g., tumor tissue) is present for analysis. Image integrity includes, for example, a detection of any out of focus images, and in the case of TMAs, analysis and detection of any split images.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

All publications, patents, and patent applications mentioned in this specification are herein incorporated by reference to the same extent as if each individual publication, patent, or patent application was specifically and individually indicated to be incorporated by reference.

1. Samples

Any cell containing sample may be analyzed by the methods of the present invention. For example, the sample may be prepared from tissues collected from patients. Alternatively, the sample may be a cell containing biological sample such as a blood sample, bone marrow sample, or a cell line. The samples may be whole-tissue or TMA sections on microscope slides. Particularly when using tissue microarrays (TMAs), samples may be arranged as "spots" or "histospots" on a slide, with each histopot corresponding to a particular sample. Such methods for preparing slide mounted tissue samples are well known in the art and suitable for use in the present invention.

2. Biomarkers

As used herein, a biomarker is a molecule that may be measured in a biological sample as an indicator of tissue type, normal or pathogenic processes or a response to a therapeutic intervention. In a particular embodiment, the biomarker is selected from the group consisting of: a protein, a peptide, a nucleic acid, a lipid and a carbohydrate. More particularly, the biomarker may be a protein. Certain markers are characteristic of particular cells, while other markers have been identified as being associated with a particular disease or condition. Examples of known prognostic markers include enzymatic markers such as, for example, galactosyl transferase II, neuron specific enolase, proton ATPase-2, and acid phosphatase. Hormone or hormone receptor markers include human chorionic gonadotropin (HCG), adrenocorticotropic hormone, carcinoembryonic antigen (CEA), prostate-specific antigen (PSA), estrogen receptor, progesterone receptor, androgen receptor, gC1q-R/p33 complement receptor, IL-2 receptor, p75 neurotrophin receptor, PTH receptor, thyroid hormone receptor, and insulin receptor.

Lymphoid markers include alpha-1-antichymotrypsin, alpha-1-antitrypsin, B cell marker, bcl-2, bcl-6, B lymphocyte antigen 36 kD, BM1 (myeloid marker), BM2 (myeloid marker), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, immunoglobulin G, immunoglobulin M, kappa light chain, kappa light chain, lambda light chain, lymphocyte/histocyte antigen, macrophage marker, muramidase (lysozyme), p80 anaplastic lymphoma kinase, plasma cell marker, secretory leukocyte protease inhibitor, T cell antigen receptor (JOVI 1), T cell antigen receptor (JOVI 3), terminal deoxynucleotidyl transferase, unclustered B cell marker.

Tumor markers include alpha fetoprotein, apolipoprotein D, BAG-1 (RAP46 protein), CA19-9 (sialyl lewisa), CA50 (carcinoma associated mucin antigen), CA125 (ovarian cancer antigen), CA242 (tumour associated mucin antigen), chromogranin A, clusterin (apolipoprotein J), epithelial membrane antigen, epithelial-related antigen, epithelial specific antigen, epidermal growth factor receptor, estrogen receptor (ER), gross cystic disease fluid protein-15, hepatocyte specific antigen, HER2, heregulin, human gastric mucin, human milk fat globule, MAGE-1, matrix metalloproteinases, melan A, melanoma marker (HMB45), mesothelin, metallothionein, microphthalmia transcription factor (MITF), Muc-1 core glycoprotein. Muc-1 glycoprotein, Muc-2 glycoprotein, Muc-5AC glycoprotein, Muc-6 glycoprotein, myeloperoxidase, Myf-3 (Rhabdomyosarcoma marker), Myf-4 (Rhabdomyosarcoma marker), MyoD1 (Rhabdomyosarcoma marker), myoglobin, nm23 protein, placental alkaline phosphatase, prealbumin, progesterone receptor, prostate specific antigen, prostatic acid phosphatase, prostatic inhibin peptide, PTEN, renal cell carcinoma marker, small intestinal mucinous antigen, tetranectin, thyroid transcription factor-1, tissue inhibitor of matrix metalloproteinase 1, tissue inhibitor of matrix metalloproteinase 2, tyrosinase, tyrosinase-related protein-1, villin, von Willebrand factor, CD34, CD34, Class II, CD51 Ab-1, CD63, CD69, Chk1, Chk2, claspin C-met, COX6C, CREB, Cyclin D1, Cytokeratin, Cytokeratin 8, DAPI, Desmin, DHP (1-6 Diphenyl-1,3,5-Hexatriene), E-Cadherin, EEA1, EGFR, EGFRvIII, EMA (Epithelial Membrane Antigen), ER, ERB3, ERCC1, ERK, E-Selectin, FAK, Fibronectin, FOXP3, Gamma-H2AX, GB3, GFAP, Giantin, GM130, Golgin 97, GRB2, GRP78BiP, GSK3 Beta, HER-2, Histone 3, Histone 3_K14-Ace [Anti-acetyl-Histone H3 (Lys 14)], Histone 3_K18-Ace [Histone H3-Acetyl Lys 18), Histone 3_K27-TriMe, [Histone H3 (trimethyl K27)], Histone 3_K4-diMe [Anti-dimethyl-Histone H3 (Lys 4)], Histone 3_K9-Ace [Acetyl-Histone H3 (Lys 9)], Histone 3_K9-triMe [Histone 3-trimethyl Lys 9], Histone 3_S10-Phos [Anti-Phospho Histone H3 (Ser 10), Mitosis Marker], Histone 4, Histone $H2A.X_S139$-Phos [Phospho Histone H2A.X (Ser139)antibody], Histone H2B, Histone H3_DiMethyl K4, Histone H4_TriMethyl K20-Chip grad, HSP70, Urokinase, VEGF R1, ICAM-1, IGF-1, IGF-1R, IGF-1 Receptor Beta, IGF-II, IGF-IIR, IKB-Alpha IKKE, IL6, IL8, Integrin alpha V beta 3, Integrin alpha V beta6, Integrin Alpha V/CD51, integrin B5, integrin B6, Integrin B8, Integrin Beta 1(CD 29), Integrin beta 3, Integrin beta 5 integrinB6, IRS-1, Jagged 1, Anti-protein kinase C Beta2, LAMP-1, Light Chain Ab-4 (Cocktail), Lambda Light Chain, kappa light chain, M6P, Mach 2, MAPKAPK-2, MEK 1, MEK 1/2 (Ps222), MEK 2, MEK1/2 (47E6), MEK1/2 Blocking Peptide, MET/HGFR, MGMT, Mitochondrial Antigen, Mitotracker Green F M, MMP-2, MMP9, E-cadherin, mTOR, ATPase, N-Cadherin, Nephrin, NFKB, NFKB p105/p50, NF-KB P65, Notch 1, Notch 2, Notch 3, OxPhos Complex IV, p130Cas, p38 MAPK, p44/42 MAPK antibody, P504S, P53, P70, P70 S6K, Pan Cadherin, Paxillin, P-Cadherin, PDI, pEGFR, Phospho AKT, Phospho CREB, phospho EGF Receptor, Phospho GSK3 Beta, Phospho H3, Phospho HSP-70, Phospho MAPKAPK-2, Phospho MEK1/2, phospho p38 MAP Kinase, Phospho p44/42 MAPK, Phospho p53, Phospho PKC, Phospho S6 Ribosomal Protein, Phospho Src, phospho-Akt, Phospho-Bad, Phospho-IKB-a, phospho-mTOR, Phospho-NF-kappaB p65, Phospho-p38, Phospho-p44/42 MAPK, Phospho-p70 S6 Kinase, Phospho-Rb, phospho-Smad2, PIM1, PIM2, PKC β, Podocalyxin, PR, PTEN, R1, Rb 4H1, R-Cadherin, ribonucleotide Reductase, RRM1, RRM11, SLC7A5, NDRG, HTF9C, HTF9C, CEACAM, p33, S6 Ribosomal Protein, Src, Survivin, Synapopodin, Syndecan 4, Talin, Tensin, Thymidylate Synthase, Tuberlin, VCAM-1, VEGF, Vimentin, Agglutinin, YES, ZAP-70 and ZEB.

Cell cycle associated markers include apoptosis protease activating factor-1, bcl-w, bcl-x, bromodeoxyuridine, CAK (cdk-activating kinase), cellular apoptosis susceptibility protein (CAS), caspase 2, caspase 8, CPP32 (caspase-3), CPP32 (caspase-3), cyclin dependent kinases, cyclin A, cyclin B1, cyclin D1, cyclin D2, cyclin D3, cyclin E, cyclin G, DNA fragmentation factor (N-terminus), Fas (CD95), Fas-associated death domain protein, Fas ligand, Fen-1, IPO-38, Mcl-1, minichromosome maintenance proteins, mismatch repair protein (MSH2), poly (ADP-Ribose) polymerase, proliferating cell nuclear antigen, p16 protein, p27 protein, p34cdc2, p57 protein (Kip2), p105 protein, Stat 1 alpha, topoisomerase I, topoisomerase II alpha, topoisomerase III alpha, topoisomerase II beta.

Neural tissue and tumour markers include alpha B crystallin, alpha-internexin, alpha synuclein, amyloid precursor protein, beta amyloid, calbindin, choline acetyltransferase, excitatory amino acid transporter 1, GAP43, glial fibrillary acidic protein, glutamate receptor 2, myelin basic protein, nerve growth factor receptor (gp75), neuroblastoma marker, neurofilament 68 kD, neurofilament 160 kD, neurofilament 200 kD, neuron specific enolase, nicotinic acetylcholine receptor alpha4, nicotinic acetylcholine receptor beta2, peripherin, protein gene product 9, S-100 protein, serotonin, SNAP-25, synapsin I, synaptophysin, tau, tryptophan hydroxylase, tyrosine hydroxylase, ubiquitin.

Cluster differentiation markers include CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw75, CDw76, CD77, CD79a, CD79b, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD114, CD115, CD116, CD117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CDw137, CD138, CD139, CD140a, CD140b, CD141, CD142, CD143, CD144, CDw145, CD146, CD147, CD148, CDw149, CDw150, CD151, CD152, CD153, CD154, CD155, CD156, CD157, CD158a, CD158b, CD161, CD162, CD163, CD164, CD165, CD166, and TCR-zeta.

Other cellular markers include centromere protein-F (CENP-F), giantin, involucrin, lamin A&C [XB 10], LAP-70, mucin, nuclear pore complex proteins, p180 lamellar body protein, ran, r, cathepsin D, Ps2 protein, Her2-neu, P53, S100, epithelial marker antigen (EMA), TdT, MB2, MB3, PCNA, and Ki67.

3. Tissue Staining

Cell containing samples may be stained using any reagent or biomarker label, such as dyes or stains, histochemicals, or immunohistochemicals that directly react with the specific biomarkers or with various types of cells or cellular compartments. Not all stains/reagents are compatible. Therefore the type of stains employed and their sequence of application should be well considered, but can be readily determined by one of skill in the art. Such histochemicals may be chromophores detectable by transmittance microscopy or fluorophores detectable by fluorescence microscopy. In general, cell containing samples may be incubated with a solution comprising at least one histochemical, which will directly react with or bind to chemical groups of the target. Some histochemicals must be co-incubated with a mordant or metal to allow staining. A cell containing sample may be incubated with a mixture of at least one histochemical that stains a component of interest and another histochemical that acts as a counterstain and binds a region outside the component of interest. Alternatively, mixtures of multiple probes may be used in the staining, and provide a way to identify the positions of specific probes. Procedures for staining cell containing samples are well known in the art.

The following, non-limiting list provides exemplary chromophores that may be used as histological imaging agents (stains or counterstains) and their target cells, cellular compartments, or cellular components: Eosin (alkaline cellular components, cytoplasm), Hematoxylin (nucleic acids), Orange G (red blood, pancreas, and pituitary cells), Light Green SF (collagen), Romanowsky-Giemsa (overall cell morphology), May-Grunwald (blood cells), Blue Counterstain (Trevigen), Ethyl Green (CAS) (amyloid), Feulgen-Naphthol Yellow S (DNA), Giemsa (differentially stains various cellular compartments), Methyl Green (amyloid), pyronin (nucleic acids), Naphthol-Yellow (red blood cells), Neutral Red (nuclei), Papanicolaou stain (which typically includes a mixture of Hematoxylin, Eosin Y, Orange G and Bismarck Brown mixture (overall cell morphology), Red Counterstain B (Trevigen), Red Counterstain C (Trevigen), Sirius Red (amyloid), Feulgen reagent (pararosanilin) (DNA), Gallocyanin chrom-alum (DNA), Gallocyanin chrom-alum and Naphthol Yellow S (DNA), Methyl Green-Pyronin Y (DNA), Thionin-Feulgen reagent (DNA), Acridine Orange (DNA), Methylene Blue (RNA and DNA), Toluidine Blue (RNA and DNA), Alcian blue (carbohydrates), Ruthenium Red (carbohydrates), Sudan Black (lipids), Sudan IV (lipids), Oil Red-O (lipids), Van Gieson's trichrome stain (acid fuchsin and picric acid mixture) (muscle cells), Masson trichrome stain (hematoxylin, acid fuchsin, and Light Green mixture) (stains collagen, cytoplasm, nucleioli differently), Aldehyde Fuchsin (elastin fibers), and Weigert stain (differentiates reticular and collagenous fibers). A comprehensive list of such stains, their description, and general use is given in R. D. Lillie, "Conn's Biological Stains", 8th ed., Williams and Wilkins Company, Baltimore, Md. (1969). Suitable mordants and compositions of the preceding are well-known to one of skill in the art.

The following, non-limiting list provides exemplary fluorescent histological stains and their target cells, cellular compartments, or cellular components if applicable: 4',6-diamidino-2-phenylindole (DAPI) (nucleic acids), Eosin (alkaline cellular components, cytoplasm), Hoechst 33258 and Hoechst 33342 (two bisbenzimides) (nucleic acids), Propidium Iodide (nucleic acids), Spectrum Orange (nucleic acids), Spectrum Green (nucleic acids), Quinacrine (nucleic acids), Fluorescein-phalloidin (actin fibers), Chromomycin A 3 (nucleic acids), Acriflavine-Feulgen reaction (nucleic acid), Auramine O-Feulgen reaction (nucleic acids), Ethidium Bromide (nucleic acids). Nissl stains (neurons), high affinity DNA fluorophores such as POPO, BOBO, YOYO and TOTO and others, and Green Fluorescent Protein fused to DNA binding protein, such as histones, ACMA, Quinacrine and Acridine Orange.

A wide variety of proprietary fluorescent organelle-specific probes are commercially available, and include mitochondria-specific probes (MitoFluor and MitoTracker dyes), endoplasmic reticulum (ER) and Golgi probes (ER-Tracker and various ceramide conjugates), and lysosomal probes (LysoTracker dyes). These probes, as well as many nonproprietary fluorescent histochemicals, are available from and extensively described in the Handbook of Fluorescent Probes and Research Products $8^{th}$ Ed. (2001), available from Molecular Probes, Eugene, Oreg.

Each cell containing sample may be co-incubated with appropriate substrates for an enzyme that is a cellular component of interest and appropriate reagents that yield colored precipitates at the sites of enzyme activity. Such enzyme histochemical stains are specific for the particular target enzyme. Staining with enzyme histochemical stains may be used to define a cellular component or a particular type of cell. Alternatively, enzyme histochemical stains may be used diagnostically to quantitate the amount of enzyme activity in cells. A wide variety of enzymatic substrates and detection assays are known and described in the art.

Acid phosphatases may be detected through several methods. In the Gomori method for acid phosphatase, a cell preparation is incubated with glycerophosphate and lead nitrate. The enzyme liberates phosphate, which combines with lead to produce lead phosphate, a colorless precipitate. The tissue is then immersed in a solution of ammonium sulfide, which reacts with lead phosphate to form lead sulfide, a black precipitate. Alternatively, cells may be incubated with a solution comprising pararosanilin-HCl, sodium nitrite, napthol ASB1 phosphate (substrate), and veronal acetate buffer. This method produces a red precipitate in the areas of acid phosphatase activity. Owing to their characteristic content of acid phosphatase, lysosomes can be distinguished from other cytoplasmic granules and organelles through the use of this assay.

Dehydrogenases may be localized by incubating cells with an appropriate substrate for the species of dehydrogenase and tetrazole. The enzyme transfers hydrogen ions from the substrate to tetrazole, reducing tetrazole to formazan, a dark precipitate. For example, NADH dehydrogenase is a component of complex I of the respiratory chain and is localized predominantly to the mitochondria.

Other enzymes for which well-known staining techniques have been developed, and their primary cellular locations or activities, include but are not limited to the following: ATPases (muscle fibers), succinate dehydrogenases (mitochondria), cytochrome c oxidases (mitochondria), phosphorylases (mitochondria), phosphofructokinases (mitochondria), acetyl cholinesterases (nerve cells), lactases (small intestine), leucine aminopeptidases (liver cells), myodenylate deaminases (muscle cells), NADH diaphorases (erythrocytes), and sucrases (small intestine).

Immunohistochemistry is among the most sensitive and specific histochemical techniques. Each sample t may be combined with a labeled binding composition comprising a specifically binding probe. Various labels may be employed, such as fluorophores, or enzymes that produce a product that absorbs light or fluoresces. A wide variety of labels are known that provide for strong signals in relation to a single binding event. Multiple probes used in the staining may be labeled with more than one distinguishable fluorescent label. These color differences provide a way to identify the positions of specific probes. The method of preparing conjugates of fluorophores and proteins, such as antibodies, is extensively described in the literature and does not require exemplification here.

Although there are at least 120,000 commercially available antibodies, exemplary primary antibodies, which are known to specifically bind cellular components and are presently employed as components in immunohistochemical stains used for research and, in limited cases, for diagnosis of various diseases, include, for example, anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, anti-CA125 antibody (ovarian and other cancers), anti-CA15-3 antibody (breast cancer), anti-CA19-9 antibody (colon cancer), anti-cerbB-2 antibody, anti-P-glycoprotein antibody (MDR, multidrug resistance), anti-CEA antibody (carcinoembryonic antigen), anti-retinoblastoma protein (Rb) antibody, anti-ras oneoprotein (p21) antibody, anti-Lewis X (also called CD15) antibody, anti-Ki-67 antibody (cellular proliferation), anti-PCNA (multiple cancers) antibody, anti-CD3 antibody (T-cells), anti-CD4 antibody (helper T cells), anti-CD5 antibody (T cells), anti-CD7 antibody (thymocytes, immature T cells, NK killer cells), anti-CD8 antibody (suppressor T cells), anti-CD9/p24 antibody (ALL), anti-CD10 (also called CALLA) antibody (common acute lymphoblasic leukemia), anti-CD11c antibody (Monocytes, granulocytes, AML), anti-CD13 antibody (myelomonocytic cells, AML), anti-CD14 antibody (mature monocytes, granulocytes), anti-CD15 antibody (Hodgkin's disease), anti-CD19 antibody (B cells), anti-CD20 antibody (B cells), anti-CD22 antibody (B cells), anti-CD23 antibody (activated B cells, CLL), anti-CD30 antibody (activated T and B cells, Hodgkin's disease), anti-CD31 antibody (angiogenesis marker), anti-CD33 antibody (myeloid cells, AML), anti-CD34 antibody (endothelial stem cells, stromal tumors), anti-CD35 antibody (dendritic cells), anti-CD38 antibody (plasma cells, activated T, B, and myeloid cells), anti-CD 41 antibody (platelets, megakaryocytes), anti-LCA/CD45 antibody (leukocyte common antigen), anti-CD45RO antibody (helper, inducer T cells), anti-CD45RA antibody (B cells), anti-CD39, CD100 antibody, anti-CD95/Fas antibody (apoptosis), anti-CD99 antibody (Ewings Sarcoma marker, MIC2 gene product), anti-CD106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salvary, glial cells), anti-tau antigen antibody (Alzheimer's disease), anti-fibrin antibody (epithelial cells), anti-keratins antibody, anti-cytokeratin antibody (tumor), anti-alpha-catenin (cell membrane), anti-Tn-antigen antibody (colon carcinoma, adenocarcinomas, and pancreatic cancer); anti-1,8-ANS (1-Anilino Naphthalene-8-Sulphonic Acid) antibody; anti-C4 antibody; anti-2C4 CASP Grade antibody; anti-2C4 CASP α antibody; anti-HER-2 antibody; anti-Alpha B Crystallin antibody; anti-Alpha Galactosidase A antibody; anti-alpha-Catenin antibody; anti-human VEGF R1 (Flt-1) antibody; anti-integrin B5 antibody; anti-integrin beta 6 antibody; anti-phospho-SRC antibody; anti-Bak antibody; anti-BCL-2 antibody; anti-BCL-6 antibody; anti-Beta Catanin antibody; anti-Beta Catenin antibody; anti-Integrin alpha V beta 3 antibody; anti-c ErbB-2 Ab-12 antibody; anti-Calnexin antibody; anti-Calreticulin antibody; anti-Calreticulin antibody; anti-CAM5.2 (Anti-Cytokeratin Low mol. Wt.) antibody; anti-Cardiotin (R2G) antibody; anti-Cathepsin D antibody; Chicken polyclonal antibody to Galactosidase alpha; anti-c-Met antibody; anti-CREB antibody; anti-COX6C antibody; anti-Cyclin D1 Ab-4 antibody; anti-Cytokeratin antibody; anti-Desmin antibody; anti-DHP (1-6 Diphenyl-1,3,5-Hexatriene) antibody; DSB-X Biotin Goat Anti Chicken antibody; anti-E-Cadherin antibody; anti-EEA1 antibody; anti-EGFR antibody; anti-EMA (Epithelial Membrane Antigen) antibody; anti-ER (Estrogen Receptor) antibody; anti-ERB3 antibody; anti-ERCC1 ERK (Pan ERK) antibody; anti-E-Selectin antibody; anti-FAK antibody; anti-Fibronectin antibody; FITC-Goat Anti Mouse IgM antibody; anti-FOXP3 antibody; anti-GB3 antibody; anti-GFAP (Glial Fibrillary Acidic Protein) antibody; anti-Giantin antibody; anti-GM130 antibody; anti-Goat a h Met antibody; anti-Golgin 97 antibody; anti-GRB2 antibody; anti-GRP78BiP antibody; anti-GSK-3Beta antibody; anti-Hepatocyte antibody; anti-HER-2 antibody; anti-HER-3 antibody; anti-Histone 3 antibody; anti-Histone 4 antibody; anti-Histone H2A X antibody; anti-Histone H2B antibody; anti-HSP70 antibody; anti-ICAM-1 antibody; anti-IGF-1 antibody; anti-IGF-1 Receptor antibody; anti-IGF-1 Receptor Beta antibody; anti-IGF-II antibody; anti-IKB-Alpha antibody; anti-IL6 antibody; anti-IL8 antibody; anti-Integrin beta 3 antibody; anti-Integrin beta 5 antibody; anti-Integrin b8 antibody; anti-Jagged 1 antibody; anti-protein kinase C Beta2 antibody; anti-LAMP-1 antibody; anti-M6P (Mannose 6-Phosphate Receptor) antibody; anti-MAPKAPK-2 antibody; anti-MEK 1 antibody; anti-MEK 2 antibody; anti-Mitochondrial Antigen antibody; anti-Mitochondrial Marker antibody; anti-Mitotracker Green FM antibody; anti-MMP-2 antibody; anti-MMP9 antibody; anti-Na+/K ATPase antibody; anti-Na+/K ATPase Alpha 1 antibody; anti-Na+/K ATPase Alpha 3 antibody; anti-N-Cadherin antibody; anti-Nephrin antibody; anti-NF-KB p50 antibody; anti-NF-KB P65 antibody; anti-Notch 1 antibody; anti-OxPhos Complex IV—Alexa488 Conjugate antibody; anti-p130Cas antibody; anti-P38 MAPK antibody; anti-p44/42 MAPK antibody; anti-P504S Clone 13H4 antibody; anti-P53 antibody; anti-P70 S6K antibody; anti-P70 phospho kinase blocking peptide antibody; anti-Pan Cadherin antibody; anti-Paxillin antibody; anti-P-Cadherin antibody; anti-PDI antibody; anti-Phospho AKT antibody; anti-Phospho CREB antibody; anti-Phospho GSK-3-beta antibody; anti-Phospho GSK-3 Beta antibody; anti-Phospho H3 antibody; anti-Phospho MAPKAPK-2 antibody; anti-Phospho MEK antibody; anti-Phospho p44/42 MAPK antibody; anti-Phospho p53 antibody; anti-Phospho-NF-KB p65 antibody; anti-Phospho-p70 S6 Kinase antibody; anti-Phospho PKC (Pan) antibody; anti-Phospho S6 Ribosomal Protein antibody; anti-Phospho Src antibody; anti-Phospho-Bad antibody; anti-Phospho-HSP27 antibody; anti-Phospho-IKB-a antibody; anti-Phospho-p44/42 MAPK antibody; anti-Phospho-p70 S6 Kinase antibody; anti-Phospho-Rb (Ser807/811) (Retinoblastoma) antibody; anti-Phsopho HSP-7 antibody; anti-Phsopho-p38 antibody; anti-Pim-1 antibody; anti-Pim-2 antibody; anti-PKC β antibody; anti-PKC β11 antibody; anti-Podocalyxin antibody; anti-PR antibody; anti-PTEN antibody; anti-R1 antibody; anti-Rb 4H1(Retinoblastoma) antibody; anti-R-Cadherin antibody; anti-RRM1 antibody; anti-S6 Ribosomal Protein antibody; anti-S-100 antibody; anti-Synaptopodin antibody; anti-Synaptopodin antibody; anti-Syndecan 4 antibody; anti-Talin antibody; anti-Tensin antibody; anti-Tuberlin antibody; anti-Urokinase antibody; anti-VCAM-1 antibody; anti-VEGF antibody; anti-Vimentin antibody; anti-ZAP-70 antibody; and anti-ZEB.

Fluorophores that may be conjugated to a primary antibody include but are not limited to Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, Fluor X, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1, 3-diazol-4-yl)-amino]caproyl] (NBD), BODIPY™, boron dipyrromethene difluoride, Oregon Green, MITOTRACKER™ Red, $DiOC_7$ (3), $DiIC_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Lissamine, Umbelliferone, Tyrosine and Tryptophan. A wide variety of other fluorescent probes are available from and/or extensively described in the Handbook of Fluorescent Probes and Research Products $8^{th}$ Ed. (2001), available from Molecular Probes, Eugene, Oreg., as well as many other manufacturers.

Further amplification of the signal can be achieved by using combinations of specific binding members, such as antibodies and anti-antibodies, where the anti-antibodies bind to a conserved region of the target antibody probe, particularly where the antibodies are from different species. Alternatively specific binding ligand-receptor pairs, such as biotin-streptavidin, may be used, where the primary antibody is conjugated to one member of the pair and the other member is labeled with a detectable probe. Thus, one effectively builds a sandwich of binding members, where the first binding member binds to the cellular component and serves to provide for secondary binding, where the secondary binding member may or may not include a label, which may further provide for tertiary binding where the tertiary binding member will provide a label.

The secondary antibody, avidin, strepavidin or biotin are each independently labeled with a detectable moiety, which can be an enzyme directing a colorimetric reaction of a substrate having a substantially non-soluble color reaction product, a fluorescent dye (stain), a luminescent dye or a non-fluorescent dye. Examples concerning each of these options are listed below.

In principle, any enzyme that (i) can be conjugated to or bind indirectly to (e.g., via conjugated avidin, strepavidin, biotin, secondary antibody) a primary antibody, and (ii) uses a soluble substrate to provide an insoluble product (precipitate) could be used.

The enzyme employed can be, for example, alkaline phosphatase, horseradish peroxidase, beta-galactosidase and/or glucose oxidase; and the substrate can respectively be an alkaline phosphatase, horseradish peroxidase, beta.-galactosidase or glucose oxidase substrate.

Alkaline phosphatase (AP) substrates include, but are not limited to, AP-Blue substrate (blue precipitate, Zymed catalog p. 61); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR™ Black (black), VECTOR™ Blue (blue), VECTOR™ Red (red), Vega Red (raspberry red color).

Horseradish Peroxidase (HRP, sometimes abbreviated PO) substrates include, but are not limited to, 2,2' Azino-di-3-ethylbenz-thiazoline sulfonate (ABTS, green, water soluble), aminoethyl carbazole, 3-amino, 9-ethylcarbazole AEC (3A9EC, red). Alpha-naphthol pyronin (red), 4-chloro-1-naphthol (4C1N, blue, blue-black), 3,3'-diaminobenzidine tetrahydrochloride (DAB, brown), ortho-dianisidine (green), o-phenylene diamine (OPD, brown, water soluble), TACS Blue (blue), TACS Red (red), 3,3',5,5'Tetramethylbenzidine (TMB, green or green/blue), TRUE BLUE™ (blue), VECTOR™ VIP (purple), VECTOR™ SG (smoky blue-gray), and Zymed Blue HRP substrate (vivid blue).

Glucose oxidase (GO) substrates, include, but are not limited to, nitroblue tetrazolium (NBT, purple precipitate), tetranitroblue tetrazolium (TNBT, black precipitate), 2-(4-iodophenyl)-5-(4-nitorphenyl)-3-phenyltetrazolium chloride (INT, red or orange precipitate), Tetrazolium blue (blue), Nitrotetrazolium violet (violet), and 3-(4,5-dimethylthiazol-2-yl)-2,5-diphenyltetrazolium bromide (MTT, purple). All tetrazolium substrates require glucose as a co-substrate. The glucose gets oxidized and the tetrazolium salt gets reduced and forms an insoluble formazan that forms the color precipitate.

Beta-galactosidase substrates, include, but are not limited to, 5-bromo-4-chloro-3-indoyl beta-D-galactopyranoside (X-gal, blue precipitate). The precipitates associated with each of the substrates listed have unique detectable spectral signatures (components).

The enzyme can also be directed at catalyzing a luminescence reaction of a substrate, such as, but not limited to, luciferase and aequorin, having a substantially non-soluble reaction product capable of luminescencing or of directing a second reaction of a second substrate, such as but not limited to, luciferine and ATP or coelenterazine and $Ca.^{2+}$, having a luminescencing product.

The following references, which are incorporated herein in their entireties, provide additional examples: J. M Elias (1990) Immunohistopathology: A practical approach to diagnosis. ASCP Press (American Society of Clinical Pathologists), Chicago; J. F. McGinty, F. E. Bloom (1983) Double immunostaining reveals distinctions among opioidpeptidergic neurons in the medial basal hypothalamus. Brain Res. 278: 145-153; and T. Jowett (1997) Tissue In situ Hybridization: Methods in Animal Development. John Wiley & Sons, Inc., New York; J Histochem Cytochem 1997 December 45(12):1629-1641.

Nucleic acid biomarkers may be detected using in-situ hybridization (ISH). In general, a nucleic acid sequence probe is synthesized and labeled with either a fluorescent probe or one member of a ligand:receptor pair, such as biotin/avidin, labeled with a detectable moiety. Exemplary probes and moieties are described in the preceding section. The sequence probe is complementary to a target nucleotide sequence in the cell. Each cell or cellular compartment containing the target nucleotide sequence may bind the labeled probe. Probes used in the analysis may be either DNA or RNA oligonucleotides or polynucleotides and may contain not only naturally occurring nucleotides but their analogs such as dioxygenin dCTP, biotin dcTP 7-azaguanosine, azidothymidine, inosine, or uridine. Other useful probes include peptide probes and analogues thereof, branched gene DNA, peptidomimetics, peptide nucleic acids, and/or antibodies. Probes should have sufficient complementarity to the target nucleic acid sequence of interest so that stable and specific binding occurs between the target nucleic acid sequence and the probe. The degree of homology required for stable hybridization varies with the stringency of the hybridization. Conventional methodologies for ISH, hybridization and probe selection are described in Leitch, et al. In Situ Hybridization: a practical guide, Oxford BIOS Scientific Publishers, Microscopy Handbooks v. 27 (1994); and Sambrook, J., Fritsch, E. F., Maniatis, T., Molecular Cloning: A Laboratory Manual, Cold Spring Harbor Press (1989).

In one embodiment, the optimal dilution of a reagent used in the present assays, such as a staining or IHC reagent, described herein may be quantitatively and automatically determined. In one embodiment, multiple dilution sets are imaged, where each of the dilution sets consist of a different respective dilution value and a respective arrangement of immunoassay staining intensity values. A respective dynamic range metric is determined for each of the multiple dilution sets relative to the respective arrangement of immunoassay staining intensity values. Having found the respective dynamic range metric, a dilution set having the numerically optimal dynamic range metric is selected and the dilution value of that dilution set is selected as being representative of an optimal dilution level of the reagent for use in the present invention.

For example, a slide-mounted tissue sample is stained with one of the dilution series of the primary antibody utilizing common immunohistochemistry techniques described above. The resulting stained specimens are each imaged using a system for viewing the detectable signal and acquiring an image, such as a digital image of the staining. Methods for image acquisition are described in more detail below. The images thus obtained are then used by the method of the invention for quantitatively determining the optimal concentration of the reagent for use in the present invention. Each tissue sample set includes a multiple different tissue samples prepared with respective titer dilution, such that different tissue sample sets have different respective titer dilutions. A quantitative analysis is performed of the pixelized images of the multiple tissue sample sets.

For each dilution set of the multiple dilution sets, a dynamic range metric and a specificity of staining are each calculated. In one embodiment of the present invention, the dynamic range metric is an average absolute deviation. In another embodiment of the present invention, the data is log transformed, and the dynamic range metric is a weighted combination of a standard deviation, a variance, and a swing ratio. The specificity of staining is calculated to maximize specific signal while minimizing noise. The specificity of staining may be computed by summing each of a set of immunoassay staining intensity values associated with a stain-specific compartment and then computing a stain specific average for the stain-specific compartment, and also summing each of a set of immunoassay staining intensity values associated with a non-stain specific compartment and then computing a non-stain-specific average. Following the calculation of these two averages, the stain specific average can be divided by the non-stain specific average to produce the specificity of staining, or a Signal to Noise Metric. In such an embodiment, a numerically large sensitivity of staining value is optimal. In another embodiment the non-stain specific average is divided by the stain specific average to produce the sensitivity of staining. In such an embodiment, a numerically small sensitivity of staining value is optimal. Following the calculation of the dynamic range metric and sensitivity of staining for each of the dilution sets, the dynamic range metric and sensitivity of staining can be combined with one another to generate a combination value for each dilution set. The resulting combination values are used to select the dilution set with the most numerically optimal combination value. Associated with the selected dilution set is a dilution value representative of an optimal dilution of a reagent. Optionally, the process performs multiple comparisons to attempt to identify multiple stain specific and non-stain specific compartments.

4. Instrument Standardization and Image Collection

Once the sample has been stained, any optical or non-optical imaging device can be used to detect the stain or biomarker label, such as, for example, upright or inverted optical microscopes, scanning confocal microscopes, cameras, scanning or tunneling electron microscopes, scanning probe microscopes, and imaging infrared detectors etc.

In one embodiment, the imaging device is a microscope system that includes an illumination source configured to illuminate a target sample, optics configured to produce a magnified image of the illuminated target sample, and a detector, such as a digital camera, configured to capture a digital image of the magnified image. Quantitative results can be obtained through manipulation of the captured digital images. Such image manipulation can include image processing techniques known to those skilled in the art. In at least some embodiments, one or more of such image capture and image manipulation is accomplished with the aid of a processor. The processor can include a computer implementing pre-programmed instructions.

For example, a tissue sample or tissue microarray can be imaged as follows: a user places the microarray on a sample stage. The user adjusts the sample stage so that the first region of interest or first histospot is at the center of the field of view and focused on by the CCD camera. The objective lens should be adjusted to the appropriate resolution, for example, a 0.6 millimeter sample can be viewed at 10× magnification. If paraffin mounted, the sample generally correspond to areas of higher light intensity than the surrounding paraffin, as assessed through various means including signals derived from the visible light scattering of stained tissues, tissue autofluorescence or from a fluorescent tag. A computer can acquire a low-resolution image (e.g. 64 pixel×64 pixel with 16 bit resolution) using computer software (Softworx 2.5, Applied Precision, Issaquah, Wash.) and an imaging platform (e.g., Deltavision). A computer automatically translates sample stage by an amount approximately equal to a field of view. The computer then acquires a second low-resolution image. This process is repeated until the computer has acquired images of the entire tissue sample or microarray. Using commercially available software, the computer then generates a composite image of the entire tissue sample or microarray.

To optionally standardize quantitative results obtained using a particular system, a system intrinsic factor can be determined to account for intensity variability of the excitation source and device variability, e.g., along the optical path. In order to achieve this, a measurement of the intensity of the excitation light source may also be obtained for example by using an inline lamp intensity measuring tool. Also a measurement of a standard or a calibration sample, e.g, a calibration microscope slide may be obtained using the particular system to define one or more optical path factors. Use of such a calibration slide is particularly useful for fluorescence-based IHC applications, in which sample fluorescent regions of the calibration slide emit radiation within respective bandwidths. The fluoresced emissions allow for characterization of an optical path at each of the one or more respective wavelengths. These measurement can be obtained simultaneously or separately.

The system also optionally includes a calibration device configured to redirect a standardized sample of the illumination source to the detector, although it has been found that the methods of the present invention do not require the use of such device. In at least some embodiments a system processor is configured to determine a correction factor for a given microscope. The correction factor can be determined from a measurement of the standardized sample of the illumination source obtained using the calibration device. The correction factor can be used (e.g., by the processor) to correct for any variations in intensity of a detected image of the target sample. For example, a calibration cube factor (CC) is determined by comparison to a universal standard cube. A light source factor (LS) is determined by summing the pixel intensities of a captured image of the calibration surface. The optical path factor (OP) is the quotient of the average total light intensity of 16 images taken for each cube/sample combination. The CC and OP factors are intrinsic to the specific hardware system being studied and need only be calculated once or at an interval where one would suspect some type of modification in the optics has occurred.

The standardized AQUA® score is shown below:

Standardized AQUA® score=Raw AQUA® score*CC factor*LS factor*OP factor where the CC and OP factors are defined upon system set-up/construction and the LS factor is measured simultaneously.

In some embodiments, a system processor is configured with instructions (e.g., software) for obtaining the calibration factor. Alternatively or in addition, the system processor is configured with instructions for using the correction factor to correct detected images. Such calibration is useful to reduce variability in intensity of the illumination source within the same microscope system, as may occur over time, and between quantitative results obtained using different microscope systems and/or different illumination sources.

5. Image Optimization a. Exposure Time

The dynamic range of pixel intensity data from the collected image may be optionally optimized to further reduce run-to-run variations, especially due to staining intensity and equipment differences that affect exposure times. The process includes capturing an image of a subject within the field of view of a camera at a first exposure time, resulting in a captured image comprising a predetermined number of pixels, wherein each pixel has an intensity value. A frequency distribution of pixel intensities of the captured image is queried to determine a region of the greatest frequency occurrence of the pixel intensities of the frequency distribution. Exposure time is then adjusted from the first exposure time to shift that region of highest frequency distribution toward the middle of the range of intensity values. In other words, the center of mass (COM) of a histogram, or frequency distribution is determined from which an adjusted exposure time is calculated to achieve an optimized dynamic range of pixel intensities. A second image of the subject can then be captured at the adjusted exposure time resulting in an image having an optimal dynamic range.

There are various ways to correct exposure for the methods described herein. One correction technique is to iteratively acquire a new image at a longer or shorter exposure time than that of the previous image until saturated pixels are minimized and the optimal dynamic range is achieved. This iterative process allows for a quick adjustment in exposure time to bring the pixel intensities down within the range of detection to optimize exposure and dynamic range. However this simplistic approach may also cause the system to overcorrect for saturated pixels and set the new exposure time too low. Therefore it is desirable to modify the aggressiveness of the correction to the exposure time to be proportional to how many pixels are saturated in the previous image.

To achieve this the new exposure time may be calculated as:

$$E = E' \times (1 - (0.5)^{(1+S)}),$$

where $$S = A \frac{CCD_x CCD_y SL}{P}$$

where E is the new exposure time, E' is the currently set exposure time, A is an aggression level, SL is the saturation limit, $CCD_x$ and $CCD_y$ represent the pixel dimensions of the captured image, and P is the count of pixels at maximum intensity. The aggression level, A, may vary but, generally, the values that one would want to choose would depend upon the amount by which images tend to be over saturated. A value of zero (0) for A represents a minimum value for which the exposure time would be halved. A practical maximum value for A is about 10, after which the exposure time will not change enough for the algorithm to be useful. In a preferred embodiment of the invention, the value for A can fall in the range of about $0 \leq A \leq 4.5$. More preferably, A is set at about 3.5.

The procedure of reducing exposure time to ensure the image is not overexposed is typically a multi-step process. In an exemplary embodiment, a 256 bin histogram is generated first for an 8-bit per pixel image obtained from the camera at the current exposure time, E'. The number of saturated pixels are identified and compared to a predetermined saturation threshold value. Then, if the image is at or below the saturation limit, the over-exposure procedure is exited. However, if the image is over exposed, the exposure time is decreased. The new, decreased exposure time can vary based upon the number of currently over exposed pixels. In an exemplary embodiment, a value S can be determined as $$S = A \frac{0.0002 \times 2048^2}{M},$$

in which A is an "aggression level" currently defined at 3.5 and M is the count of pixels at maximum intensity. Then, the next exposure time E is derived as follows:

$$E = E' - E_{0.5}^{1+S}$$

When the number of over exposed pixels is much greater than the saturation limit, $E \approx E' - 0.5E'$ (e.g., the exposure time would be halved). The minimum amount of change to the current exposure time occurs when the number of over saturated pixels is very nearly equal to the saturation limit, in which case $E \approx E' - 0.088E'$. Thus, because the algorithm is exited when the image is at or below the saturation limit, the number of saturated pixels will never equal the saturation limit. The procedure of reducing exposure time can be repeated in an iterative manner until the amount of overexposure is within a chosen threshold, or until a maximum number of iterations has been accomplished. In either instance the over-exposure correction routine is then exited.

An alternative and equally viable process for correcting for overexposure is to acquire a new image at a minimum exposure time, then proceed with optimizing the exposure time by calculating the COM and bringing it within range of the midpoint, as described above.

b. Image Validation

The quality of the image may be automatically assessed and optimized to reduce variations due to one or more factors selected from stain uniformity, stain quality, tissue sufficiency, tissue sample position, signal saturation, focus, and signal intensity. Thus, images can be corrected for false readings due to no sample, too little sample, debris, multiple sample or "split image" (in the case of TMA analysis) and poor focus such that invalid images may be excluded from subsequent data analysis. Each stain may be validated independently from other stains on the same or different images. These assessments and optimizations may be performed automatically by an image-processing program with particular threshold values fixed in the program or provided by the user.

To optionally determine stain uniformity across the slide or at least the imaged portion of the slide, the intensity values of vertical columns of the image pixels are combined along the respective column and plotted across the x-axis. The combination can be a straightforward addition of pixel intensity values along the column. Alternatively or in addition, the combination can be a statistically arrived at value, such as an average intensity value of all of the pixels in the column. For example, with an image using 8 bits to represent intensity, there are 256 possible pixel intensity values for each pixel. The pixel intensity values span a range from black (e.g., "0") to white (e.g., "255"). Values in between black and white are associated with varying shades of gray. The relative maximum intensity values, or peak values, may be compared between different regions of the image to determine stain uniformity and positional bias. If a bias is found, the image may be excluded from further analysis.

To optionally determine stain quality, the staining intensity of the compartment specific stain inside the compartment is measured by analyzing pixels intensity of the digital image that are identified as part of the compartment. For example to measure the stain quality of a nuclear stain, total stain intensity within the nuclear cellular compartment may be formulated as a combination, such as a sum of the intensities of pixels identified as representing nuclei. Total stain intensity outside of the nuclear cellular compartment can be similarly formulated as a sum of the intensities of pixels identified as not nuclear. The two values for nuclei and non-nuclear are compared. For example, the two values can be combined in a ratio, the single value of the ratio indicative of the comparison. For example, the combined nuclei intensity can be divided by the combined non-nuclear intensity by the image processing program to provide a tissue stain quality ratio. A low ratio, such as a ratio approaching 1, is indicative of poor staining quality or poor tissue integrity. An acceptable minimum staining quality threshold can be fixed or settable by a user. Such samples identified as failing to meet the minimum staining threshold can be excluded from the data set and from further analysis by the validation program.

Tissue sufficiency may be analyzed by counting the pixels of an image with signal intensities above a threshold intensity then determining if the total number of positive pixels meets a minimum criterion for sufficient tissue. Likewise, the percent positive pixels to the total may be used as the criterion.

When analyzing tissue microarrays, tissue sample position may be assessed by calculating the average pixel intensity in each of multiple different sections identified within the field of view. Individual samples or histospots must be identified to determine position, which may be used by comparing the position of the edge of the sample with the center of the sample. The sample edge is determined based on pixel intensity of rectangular areas to assess if the centered properly, and the central pixel intensity is measured to determine if the edges are not due more than one sample. Sample edge detection may be performed using a discrete differentiation operator, such as a Sobel edge detector, or any other number of edge detectors well-known in the art. Incorrectly positioned samples or split spots containing more than one target may then be identified and excluded from further analysis.

Focus of the sample may be assessed, such as by determining a kurtosis value for the pixel intensities of the image. The staining intensity values of pixels in a digitized image can be plotted in a histogram. The distribution can be analyzed as an indication of focus. An in focus image will typically have a pixel intensity distribution with a relatively sharp, defined peak (higher kurtosis) compared to an out of focus image which will have a pixel intensity distribution with a flattened peak (lower kurtosis). The sharpness or flatness of such a distribution can be represented in a single value, such as a kurtosis value. A higher kurtosis value is indicative of a relatively sharp defined peak; whereas, a lower kurtosis value is indicative of a flattened peak.

Kurtosis is a measure of whether the data are peaked or flat relative to a normal distribution. That is, data sets with high kurtosis tend to have a distinct peak near the mean, decline rather rapidly, and have heavy tails. Data sets with low kurtosis tend to have a flat top near the mean rather than a sharp peak. For univariate data $Y_1, Y_2, \ldots, Y_N$, the formula for kurtosis is:

$$\text{kurtosis} = \frac{\sum_{i=1}^{N}(Y_i - \overline{Y})^4}{(N-1)s^4}$$

where $\overline{Y}$ is the mean, s is the standard deviation, and N is the number of data points. Excess kurtosis can be defined as $$\text{kurtosis} = \frac{\sum_{i=1}^{N}(Y_i - \overline{Y})^4}{(N-1)s^4} - 3$$

so that the standard normal distribution has a kurtosis of zero. Positive kurtosis indicates a "peaked" distribution and negative kurtosis indicates a "flat" distribution. Images with negative kurtosis may then be excluded from further analysis.

Signal intensity may be assessed by sorting the signal intensity data measured from images acquired in each relevant channel for each histospot and identifying the number of samples with low staining intensities. Such samples may be excluded from further analysis.

6. AQUA® Scoring

Once the image is optimized and validated, with any invalid histospots or images removed, the image is virtually masked, three dimensional approximations of cells in the sample may be generated, and biomarkers are associated with subcellular compartments of individual cells. One such algorithm for automatically performing these tasks is the Automated QUantitative Analysis platform (AQUA® platform). This technique is also described in U.S. Pat. No. 7,219,016 and Camp et al., 2002 Nature Medicine 8(11)1323-1327 which are both specifically incorporated herein by reference in their entirety. However, for the first time, automation of each step is described herein, increasing the ease and reproducibility of this analysis.

In one embodiment tissue samples are stained with markers that define, for example, the cellular compartments of interest and the specific target (or targets) being studied. Pixel-based local assignment for compartmentalization of expression (PLACE) is the key algorithm that functions to effectively segment image pixels for the purpose of expression compartmentalization. A critical step in this algorithm is the setting of intensity thresholds that are used to delineate background or non-specific pixels from signal-specific pixels. Images that have been "masked" in this way are subsequently combined in a mutually-exclusive fashion such that pixels above the thresholds are assigned to specific cellular compartments. Once pixels have been assigned to each compartment, the signal for the target biomarker can then be averaged over all of the pixels assigned to a given compartment, which is the AQUA® score for that sample.

For example, a tumor-specific mask may be generated by manually thresholding the image of a marker (cytokeratin) that differentiates tumor from surrounding stroma and/or leukocytes. This creates a binary mask (each pixel is either 'on' or 'off'). Thresholding levels are verified, and adjusted if necessary, by checking a small sample of images and then remaining images are automatically masked using the single determined threshold value. All subsequent image manipulations involve only image information from the masked area. Off target specific images may be clustered to iteratively adjust pixel intensities of nonstandard masked targets. The dilate image processing technique allows for a spatial low pass filter to fill in nearest-neighbor pixels that are surrounded by pixels included in the mask. The erode image processing technique allows for a spatial high pass filter to remove pixels that are not contiguous with the mask or that form structures that are contrary to structures expected for a given slide-mounted tissue sample. Such adjustments allow inclusion of valid but nonconforming samples that may otherwise be excluded from further analysis.

Next, the signal to noise ratio may be enhanced by correcting for background noise. For example, two images (one in-focus, one out of focus, e.g., taken 6 μm deeper into the sample) are taken of the compartment-specific tags and the target marker. The out of focus image acts as a spatial low pass filter that provides a background value. For example, percentage of the out-of-focus image is subtracted from the in-focus image, based on a pixel-by-pixel analysis of the two images, such as by using an algorithm called RESA (Rapid Exponential Subtraction Algorithm). The RESA algorithm enhances the interface between areas of higher intensity staining and adjacent areas of lower intensity staining, allowing easier assignment of pixels to background and adjacent compartments. Finally, the PLACE algorithm assigns each pixel in the image to a specific cellular compartment. Pixels that cannot be accurately assigned to a compartment within a user-defined degree of confidence are discarded. For example, pixels where the nuclear and cytoplasmic pixel intensities are too similar to be accurately assigned are negated (for example, comprising <8% of the total pixels). Once each pixel is assigned to a cellular compartment (or excluded as described above), the signal in each location is summed to generate the AQUA® score for that sample, as shown in the following equation:

$$AQ = \left(\frac{1}{\sum C_i}\right)\left(\sum T_i C_i\right)$$

where AQ is the raw AQUA® score, $T_i$ is the $i^{th}$ target intensity, also known as power density, and $C_i$ is the $i^{th}$ cell compartment probability. These data are saved and can subsequently be expressed either as a percentage of total signal or as the average signal intensity per compartment area.

Preferably, the AQUA® score may be automatically normalized, for example, by clustering, to assign pixels to a particular cellular compartment based on intensity data. This clustering allows for further removal of background noise, assignment of specific pixels to a given compartment and probabilistic assignment of pixels to each compartment where there may be overlapping signals. Once pixels are assigned to each compartment (or discarded in the case of noise) the associated target signals can be measured, for example summed and a score calculated.

The assignment is preferentially determined on an image-to-image basis, rather than setting universal criteria. Furthermore, pixel assignment (e.g., Cy3/Cytokeratin pixels to cytoplasm) is also a function of other compartment images such that consideration is given to the status of pixels in other compartment images. In one embodiment one image is of a first stain that specifically labels a first compartment (e.g., a Cy3/cytokeratin image, representing the cytoplasmic compartment) and a second image is of a second stain that specifically labels a second compartment (e.g., DAPI image, representing the nuclear compartment) and pixel assignments are based on four criteria:

1.) Low intensity in both first and second image (e.g., DAPI and Cy3): BACKGROUND: REMOVE 2.) High second stain (e.g., DAPI) intensity relative to first stain (Cy3) intensity: SECOND COMPARTMENT (e.g., NUCLEAR)

3.) High first stain (e.g., Cy3) intensity relative to second stain (e.g., DAPI) intensity: FIRST COMPARTMENT (e.g., CYTOPLASMIC)

4.) High second stain and first stain (e.g., DAPI and Cy3) intensity: INDETERMINANT: REMOVE Clustering is a mathematical algorithmic function whereby centroids within data sets are defined by relative distances of each data point to one another, as determined, for example, by Euclidean or log-likelihood distance. While not wishing to be bound by theory, it is believed that clustering pixel intensities from at least two images (e.g., DAPI and Cy3), could result in centroids that define pixels as described, at least, by the above criteria. Because clustering is objective and can be performed individually on each image, clustering is a reliable method for assignment of pixels to compartments, independent of operator intervention.

In another embodiment, pixels containing signal indicative of both the first and second stain are assigned to compartments by the following method. Every pixel in acquired images has three attributes intensity contribution from compartment marker A, intensity contribution from compartment marker B and an intensity contribution from the target or biomarker of interest. These intensities are measured in their respective fluorescence channels per the experimental configuration. To avoid experimental bias, the target intensity is not manipulated in this current method. Thus, the data for the two compartment attributes can be illustrated in a two dimensional plot schematically.

Pixels with a strong bias towards either of the axes can be assigned to that compartment (e.g., pixels in regions A and B could be absolutely assigned to compartments A and B respectively). Pixels near the origin represent low intensities for both channels and can be discarded as background along with outlier pixels that have high intensity but similar values. Pixels that remain in region A/B can then be assigned to each compartment based on probability. This assignment allows target signal in those pixels to be distributed across both compartments based on the probability characterization.

To define the regions described above, for example, for every image, clustering is used to determine three centroids in the data. This method is fully automated and does not require any operator decisions to proceed. The analysis is accomplished by performing k-means clustering on three centroids using Euclidean distances.

The data are then analyzed as follows: (i) Background and outlier pixels are discarded from further calculation. A pixel is defined as background if its distance to the origin is less than twice that of the background centroid distance to the origin. A pixel is define as an outlier if its intensity exceeds the value defines by the line or plane defined by the outermost centroids; (ii) Pixels in regions A and B are assigned exclusively to those two compartments; (iii) Pixels in the triangular region A/B are then assigned a probability value that allows them to essentially be distributed in multiple compartments. This probability value can be calculated based on distance from the two regions A and B, or, using a shape function that will also assign a probability of each pixel having a contribution from the background region by examining each pixel's distance from the three vertices given by the centroids; (iv) With all pixels assigned, the associated target scores can be summed up for each compartment and a score calculated using standard methods:

$$\frac{\sum_{i}^{\#pixels} Int_i^* P_i}{\sum_{i}^{\#pixels} P_i}$$

where Int is the intensity of the pixel, P is the probability of the pixel being assigned to a particular compartment (ranging from 0 to 1).

Cutpoints are established using algorithms to separate samples into groups with specific features, such as samples containing tissues with different biomarker expression levels for one or more biomarker, as described in more detail in McCabe et al., J. Natl. Canc. Inst. (2005) 97(24):1808-1815, which is hereby incorporated by reference in its entirety. By reducing sample biomarker quantification results using the methods of the present invention, intra-group variation is minimized, differences between groups are maximized and more easily identified. For instance, a high expression level of a biomarker, represented by a high AQUA® score, may be more tightly correlated with aggressive disease and reduced survival, whereas a lower AQUA® score is not. By reliably distinguishing the two groups, the correlation between a biomarker and disease becomes more clear. Thus, AQUA® scores generated using the methods of the invention provide a reliable assay for comparing sample groups such that the biomarker may be more specifically correlated with the particular characteristics, leading to more reliable diagnosis and prognosis estimation on an individual sample.

7. Reproducibility

Because the variability of AQUA® scores is reduced through automatic instrument standardization, such as exposure optimization, as well as through normalization of the raw AQUA® scores by clustering, as well as by optionally improved image validation, the sensitivity and reproducibility of the assay is enhanced. For example, in one embodiment, the data signal attributed to two or more cell compartments can be more reliably distinguished. In a further embodiment data signal can be distinguished with at least about 90% confidence interval. In a further embodiment, the data signal can be distinguished with about a 95% confidence interval. In a further embodiment, the data signal can be distinguished with about a 99% confidence interval.

The normalized AQUA® score provides a more reproducible cutpoint determination, leading to greater agreement of sample classification between runs. In one embodiment, the assay provides for a greater than 85% concordance for sample classification from one run to another for each sample. In a further embodiment, the assay provides for a greater than 90% concordance for sample classification from one run to another for each sample. In a further embodiment, the assay provides for a greater than 95% concordance for sample classification from one run to another for each sample. In a further embodiment, the assay provides for a greater than 99% concordance for sample classification from one run to another for each sample.

The normalized AQUA® score provides a more reproducible quantified measure of biomarker expression. In one embodiment, the quantified measure of biomarker expression level has a reproducibility above 80%. In a further embodiment, the quantified measure of biomarker expression level has a reproducibility above 90%. In a further embodiment, the quantified measure of biomarker expression level has a reproducibility above 95%. In a further embodiment, the quantified measure of biomarker expression level has a reproducibility above 99%. In a further embodiment, the quantified measure of biomarker expression level has a reproducibility from about 85% to about 99%. In a further embodiment, the quantified measure of biomarker expression level has a reproducibility from about 90% to about 99%. In a further embodiment, the quantified measure of biomarker expression level has a reproducibility from about 90% to about 97%.

In one embodiment, the normalized AQUA® score provides a quantified measure of biomarker expression having a coefficient of variation (% CV) below 20%. In a further embodiment, the normalized AQUA® score provides a quantified measure of biomarker expression having a coefficient of variation (% CV) below 10%. In a further embodiment, the normalized AQUA® score provides a quantified measure of biomarker expression having a coefficient of variation (% CV) below 5%. In a further embodiment, the normalized AQUA® score provides a quantified measure of biomarker expression having a coefficient of variation (% CV) from about 1% to about 20%. In a further embodiment, the normalized AQUA® score provides a quantified measure of biomarker expression having a coefficient of variation (% CV) from about 5% to about 15%. In a further embodiment, the normalized AQUA® score provides a quantified measure of biomarker expression having a coefficient of variation (% CV) from about 4% to about 7%.

Thus, normalized AQUA® scores provides a reliable assay for comparing sample groups such that the biomarker may be more specifically correlated with the particular characteristics, leading to more reliable diagnosis and prognosis estimation.

EXAMPLES

Example 1

Standardization of HER2 Analyses Using Automated Aqua® Technology

Materials and Methods

Cohort Description and TMA Construction

A large breast cancer cohort in tissue microarray (TMA) format was employed in these studies in order to test standardization techniques. This cohort from the Yale Tissue Microarray Facility (YTMA49) has been described in detail previously (Dolled-Filhart M, et al. Cancer Res. (2006) 66:5487-94). Briefly, the breast cohort (n=669) of invasive ductal carcinoma serially collected from the Yale University Department of Pathology from 1961 to 1983. Also on the array is a selection of normal tissue and cell line controls. The mean follow-up time is 12.8 years with a mean age of diagnosis of 58.1 years. This cohort contains approximately half node-positive and half node-negative specimens. Detailed treatment information was not available for this cohort.

Immunohistochemical/Immunofluoresence Tissue Staining

Chromagen-based immunohistochemical staining and scoring for cases in YTMA49 was performed previously as described (Camp R L, et al. Cancer Res. (2003) 63:1445-1448, which is hereby incorporated by reference in its entirety). YTMA49 was stained using a modified indirect immunofluorescence protocol (Camp R L, et al. Nat. Med. (2002) 8:1323-1327, which is hereby incorporated by reference in its entirety). In brief, pre-cut paraffin-coated tissue microarray slides were de-paraffinized and antigen-retrieved by heat-induced epitope retrieval in 10 mM Tris (pH 9.0). Using an auto-stainer (LabVision, Fremont, Calif.), slides were pre-incubated with Background Sniper (BioCare Medical, Concord, Calif.). Slides were then incubated with primary antibodies against HER2 (Dako (Carpinteria, Calif.), rabbit polyclonal, 1:8000 dilution) and pan-cytokeratin (rabbit polyclonal, 1:200 dilution, DAKO, Carpinteria, Calif.) diluted in DaVinci Green (BioCare Medical, Concord, Calif.) for 1 hour at RT.

Slides were washed 3×5 min with 1×TBS containing 0.05% Tween-20. Corresponding secondary antibodies were diluted in Da Vinci Green and incubated for 30 minutes at room temperature. These included either antibodies directly conjugated to a fluorophore for anti-cytokeratin (Alexa 555-conjugated goat anti-rabbit; 1:100, Molecular Probes, Eugene, Oreg.), and/or conjugated to a horseradish peroxidase (HRP) via, anti-mouse or rabbit Envision (Dako, Carpinteria, Calif.)). Slides were again washed 3×5 min with TBS containing 0.05% Tween-20. Slides were incubated with a fluorescent chromagen amplification system (Cy-5-tyramide, NEN Life Science Products, Boston, Mass.) which, like DAB, is activated by HRP and results in the deposition of numerous covalently associated Cy-5 dyes immediately adjacent to the HRP-conjugated secondary antibody. Cy-5 (red) was used because its emission peak is well outside the green-orange spectrum of tissue auto-fluorescence. Slides for automated analysis were cover slipped with an anti-fade DAPI-containing mounting medium (ProLong Gold, Molecular Probes, Eugene, Oreg.).

Microscopy System and Image Acquisition

The PM2000™ system, commercialized by HistoRx, Inc. (New Haven, Conn.), is based on a system described previously (Camp et al., 2002, supra). In brief, it is comprised of the Olympus BX51 epi-fluorescence microscope (Olympus America, Inc., Center Valley, Pa.) which is equipped with a motorized nosepiece to control selection of objectives (e.g., 4×, 10×, 20×, 40×, and 60×); a motorized filter turret to control selection of different filter cubes (e.g., DAPI, Cy2, Cy3, Cy5, and Cy7 or equivalent wavelengths); a motorized stage to control stage movements (Prior Scientific Inc., Rockland, Mass.); an X-Cite 120 mercury/metal halide light source (EXFO Life Sciences & Industrial Division, Ontario, Candada); and a QUANTFIRE monochromatic digital camera (Optronics, Inc., Goleta, Calif.).

Automated image capture was performed by the HistoRx PM-2000 using the AQUAsition™ software package. High resolution, 8 bit (resulting in 256 discrete intensity values per pixel of an acquired image) digital images of the cytokeratin staining visualized with Cy3, DAPI, and target (HER2) staining with Cy5 were captured and saved for every histospot on the array. Pixels were written to image files as a function of power (Power (P)=((Pixel Intensity/256)/exposure time) in order to help compensate for experimental variations in staining intensity and exposure times.

AQUA® Score Generation

Images were validated for percent area tumor (tumors showing <5% area/field were redacted), out-of-focus, and debris. Of the 669 tumor samples on YTMA49, 86 samples were redacted (12.8%) leaving a 583 samples for subsequent scoring and analysis. Compartment specific AQUA® scores for HER2 for each histospot were generated based on the PLACE (pixel-based locale assignment for compartmentalization of expression algorithm) algorithm as described previously (Camp et al., 2002, supra). To remove operator-to-operator bias for threshold setting, an unsupervised pixel-based clustering algorithm for optimal image segmentation was used in the PLACE algorithm as described elsewhere in this application.

Instrument Standardization

For AQUA® score standardization for instrument variability, three calibration factors were developed: calibration cube factor (CC factor), light source factor (LS factor), and Cy5 optical path factor (OP factor). Calculation of these factors is based on pixel intensity measurements given by images acquired under described conditions. All factors rely on a specialized filter cube (calibration cube) designed whereby light is reflected directly from the light source to the camera via white filter paper attached to the objective-end of the filter cube. To account for variations in the different cube constructions, calibration cubes for each machine were standardized by calculating the percentage of the average total light intensity compared to average total light intensity of a "gold standard" calibration cube (producing the CC factor). This is a constant factor which is calculated and maintained for each cube, and thus each microscope system with that cube installed. The light source factor is calculated for each histospot acquired and is the total light intensity as measured by the calibration cube divided into a constant (100,000). The optical path factor accounts for the amount of light passed through a specific microscope objective/filter combination relative to the measured incoming light intensity. For these measurements, a standard sample is required that can be transferred between different machines and maintain reproducibility in its construction. A commercially available blue fluorescent standard slide was selected for this purpose (Omega Optical Inc., Brattleboro, Vt.). Standardization was performed as described herein previously.

Statistical Analysis

For analysis, AQUA® scores were $Log_2$ transformed. Statistical analysis and output was performed using SPSS 15.0 (SPSS Inc, Chicago, Ill.) unless otherwise noted. Optimal cut-points for continuous HER2 AQUA® data for 5-year disease-specific death were generated as a function of survival using the software package X-Tile as described previously (Camp R L, et al., Clin. Cancer Res. (2004) 10:7252-7259, which is hereby incorporated by reference in its entirety). X-tile performs Monte Carlo simulations (e.g. cross-validation (Raeside DE. Phys Med Biol. (1976) 21:181-97, which is incorporated by reference in its entirety) to produce corrected P-values to assess statistical significance of data generated by multiple cut-points. The software also generates training/validation subsets for additional P-value estimation. Agreement percentages with 95% confidence intervals for 2×2 contingency tables were determined using the web-based tool, JavaStat, for 2-way contingency table analysis.

Results

HER2 Immunofluorescence Staining

Fluorescent stains were multiplexed to compartmentalize and measure expression of specific biomarkers. For HER2, only pixels (Cy5) within the cytokeratin-derived (epithelium specific) compartment (Cy3) were considered for analysis, thus differentiating tumor from stromal HER2 signal as well as membrane/cytoplasm from nuclear HER2 signal. As described, only HER2 pixels that coincided with cytokeratin pixels were used to generate an AQUA® score.

AQUA® Score Correlation with Traditional IHC Scoring Methods

Figure 3:
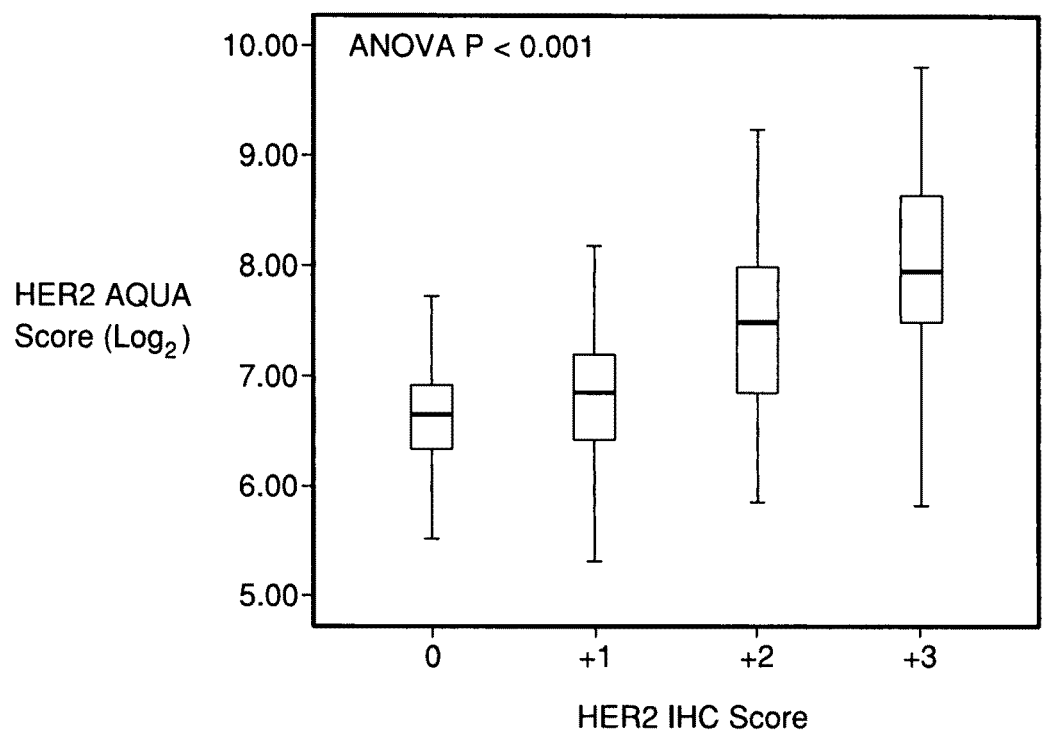
FIG. 3 is a box plot of $Log_2$-transformed HER2 AQUA® scores (y-axis) categorized by traditional IHC scoring (x-axis) for 543 cases with both AQUA® and IHC scoring information. One-way ANOVA analysis for comparison of means across all categories was significant (P<0.001). Post-hoc analysis using Tamhane's T2 statistic for multiple comparisons shows significant differences between each category (all P-values <0.05).

HER2 AQUA® scores showed a moderate, but highly significant correlation with categorical IHC scoring methods (0, +1, +2, and +3) with Spearman's Rho value of 0.46 ($P<0.001$). Multinomial regression analysis (for comparison of categorical versus continuous data) showed a highly significant correlation ($P<0.001$) with a pseudo-R value of 0.56. FIG. 3 categorizes HER2 AQUA® scores as a function of IHC scores using a box plot. Although there was a highly significant difference in population mean (ANOVA $P<0.001$), because AQUA® provides a continuous expression score, significant overlap of AQUA® scores was observed across the range of traditional categorical scoring.

Normalized HER2 Expression Scores

Figure 4A:
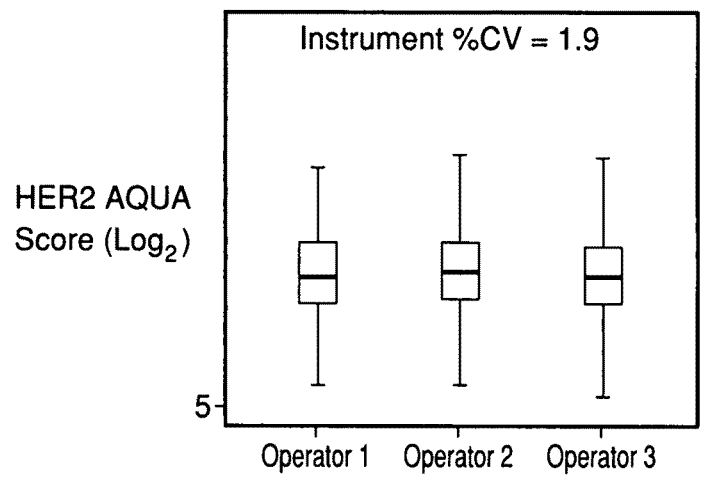
FIGS. 4A-C show box plots comparing normalized $Log_2$-transformed HER2 AQUA® scores across instruments (A), operators (B), and staining runs (C) for 583 cases with indicated averaged % CV for all cases.
Figure 4B:
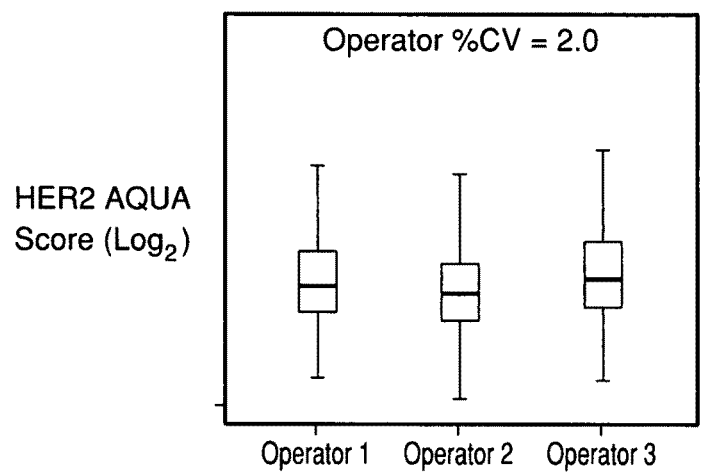
Figure 4C:
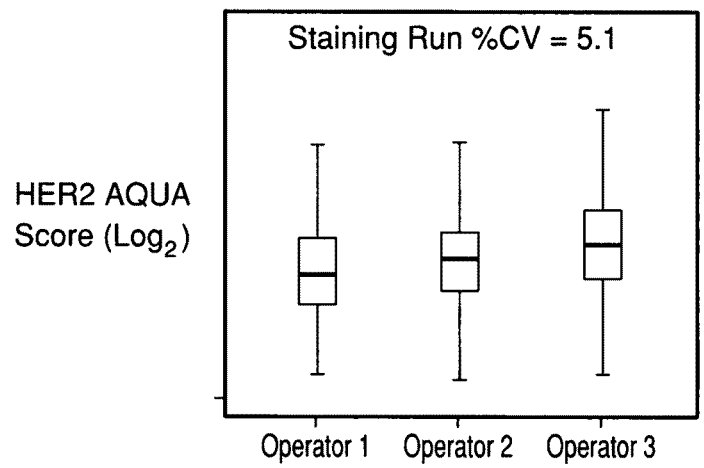

Three serial sections of a cohort (n=669) of invasive breast cancers were fluorescently stained for HER2 as described in Materials and Methods. The first serial section was used for AQUA® score generation across three different instruments and three different operators. The second and third serial sections were stained on separate days to assess run-to-run variability. FIG. 4 gives box plots showing normalized AQUA® score distributions for each indicated acquisition parameter (instrument (FIG. 4A), operator (FIG. 4B), and independent staining runs (FIG. 4C)). For 583 patient samples, the average percent coefficient of variation (% CV) was 1.8% (min=0.04%; max=10.7%) across instruments, 2.0% (min=0.06%; max=15.6%) across operators, and 5.1% (min=0.12%; max=29.7%) across independent staining runs. These % CVs rival that of in vitro immunoassays such as ELISA (Butler et al. J Immunoassay. (2000) 21:165-209).

Positive/Negative Concordance

Figure 5A:
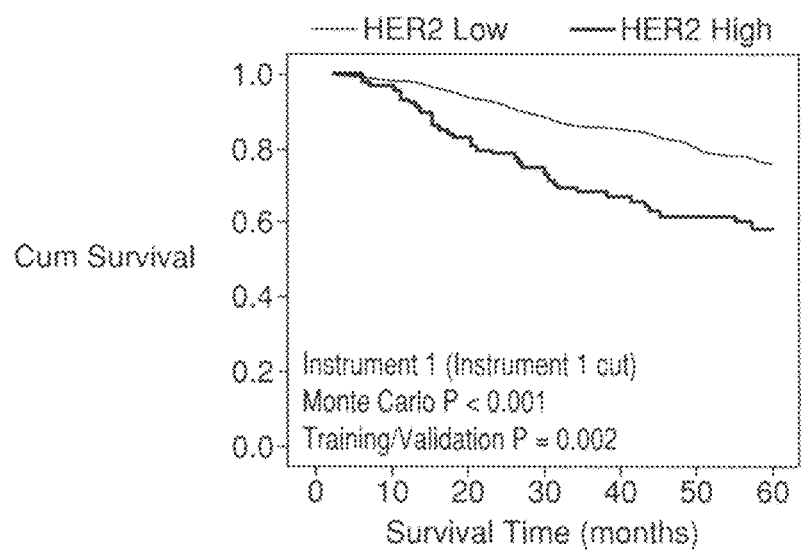
FIGS. 5A-C show Kaplan-Meier 5-year disease-specific survival analysis plots for (A) X-tile determined cut-point for instrument 1 HER2 AQUA® scores dividing the population into HER2 low (84.5%) and HER2 high (15.5%) showing a significant [Monte Carlo P<0.001; training/validation P=0.002] 17.8% reduction in cumulative survival from 75.7-57.9%. This cut-point was applied to instrument 2 (B) and instrument 3 (C) with significance (P<0.001 and P=0.004 respectively) and equivalent curve shape and composition for instrument 2 [HER2 low (83.6%); HER2 high (16.4%); 15.4% reduction in cumulative survival from 75.5-60.1%] and instrument 3 [HER2 low (84.9%); HER2 high (14.1%); 13.5% reduction in cumulative survival from 74.9-61.4%].
Figure 5B:
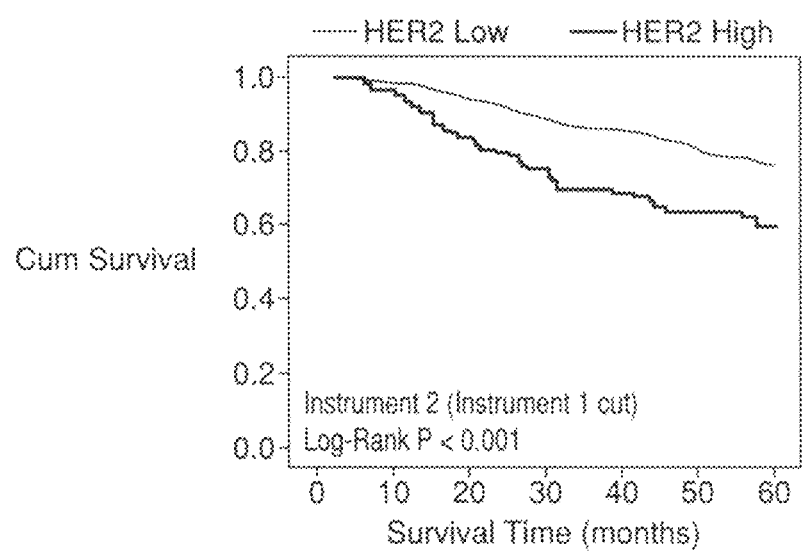
Figure 5C:
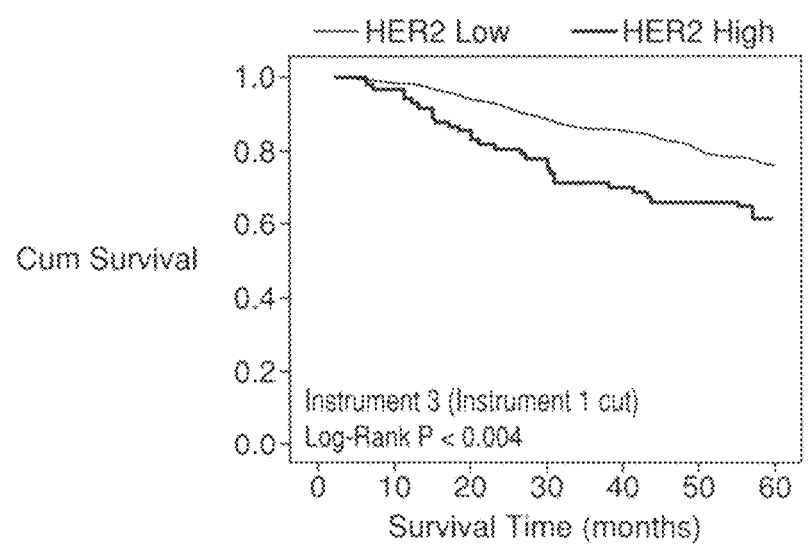

A critical parameter for HER2 testing in the clinical laboratory is the ability to reproducibly classify patients as positive or negative. Using survival as a surrogate marker for positive/negative classification 22, an optimal AQUA® score cut-point was established using X-tile 19 for normalized HER2 AQUA® scores produced for instrument 1, operator 1, and staining run 1. FIG. 5A shows Kaplan-Meier survival analysis of positive/negative HER2 classification for instrument 1. As described in Materials and Methods, the cut-point was validated with significance by Monte Carlo simulation (P<0.001) and training/validation subsets (P=0.002). This validated cut-point was applied to AQUA® scores generated on instruments 2 and 3 with significance, P<0.001 and P=0.004 respectively (FIGS. 5B and 5C). Similar reproducibility was observed across independent operator and staining run acquisitions with P-values all ≤0.01 (data not shown).

Current ASCO-CAP guidelines are suggesting laboratories achieve 95% positive/negative concordance for current HER2 assay methodologies (Wolff A C et al, Arch Pathol Lab Med. (2007) 131:18). A recent study shows that for HER2 IHC-based scoring, concordance between observers ranges from 54-85%, falling short of these guidelines (Hameed et al; in press; direct communication). Positive/negative concordance for normalized AQUA® scoring across instruments, operators, and staining days was examined using the cut-points established above. As shown in FIG. 6, overall concordance ranged from 94.5% (Instrument 1 to Instrument 3; FIG. 6B) to 99.3% (Operator 1 to Operator 2; FIG. 6C). These analyses include all cases including those that would be considered equivocal.

Figure 7A:
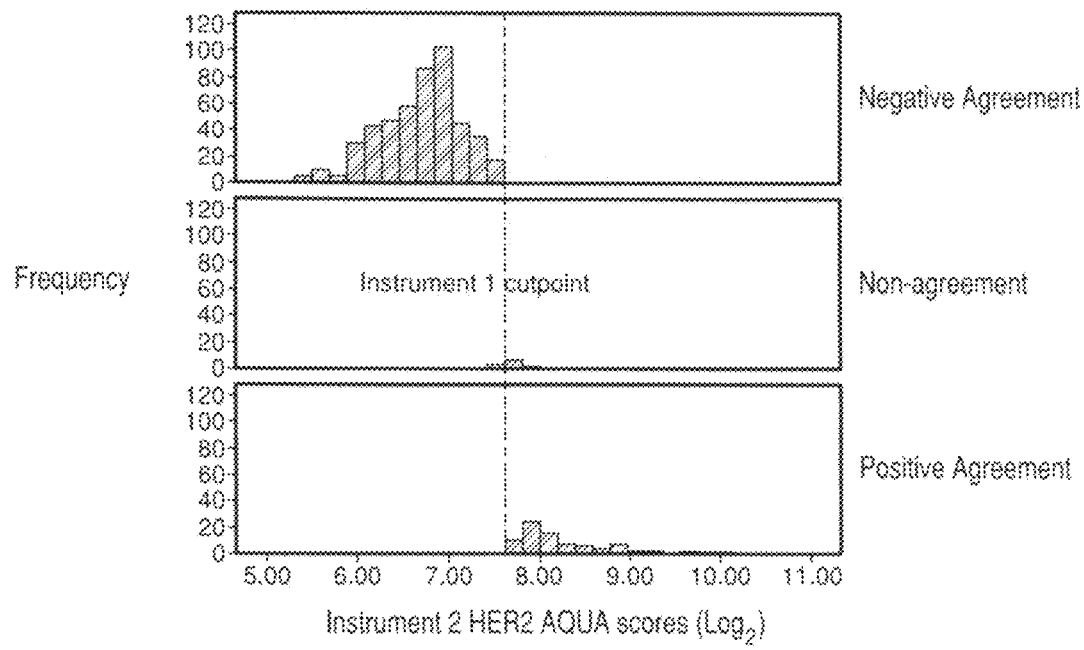
FIGS. 7A-C are frequency distributions separated into negative agreement, positive agreement, and non-agreement cases for (A) instrument 2 (AQUA® scores) to instrument 1 (cut-point); (B) operator 2 (AQUA® scores) to operator 1 (cut-point); and (C) run 2 (AQUA® scores) to run 1 (cut-point) to demonstrate where disagreement occurs within the population of breast cancer cases. Cases which disagree reside in and around the indicated cut-points and do not span over the entire distribution.
Figure 7B:
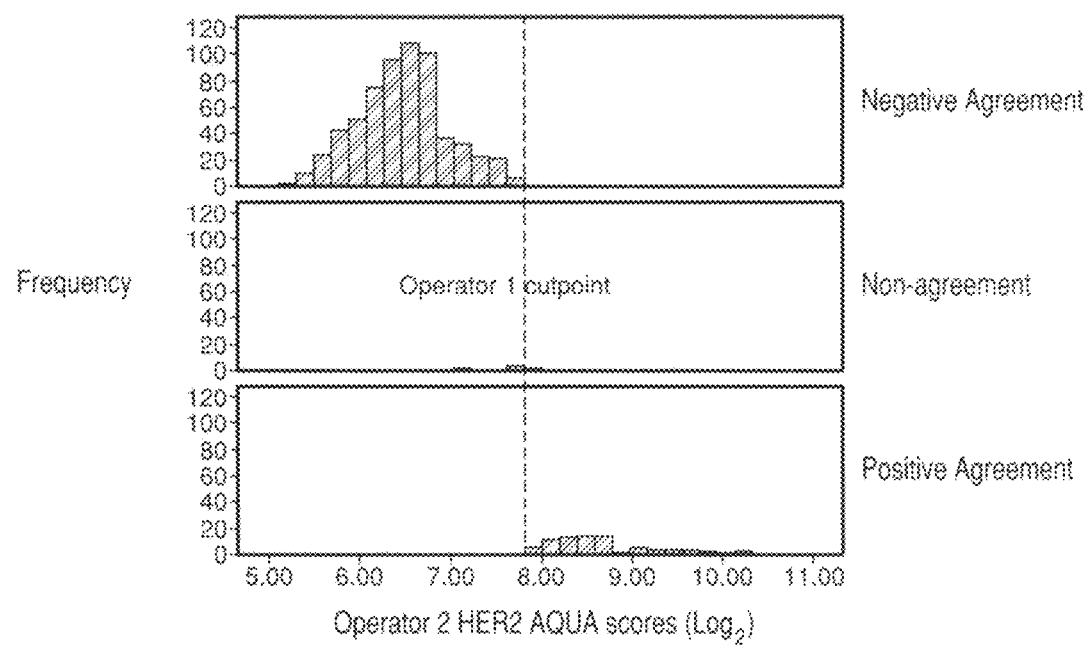
Figure 7C:
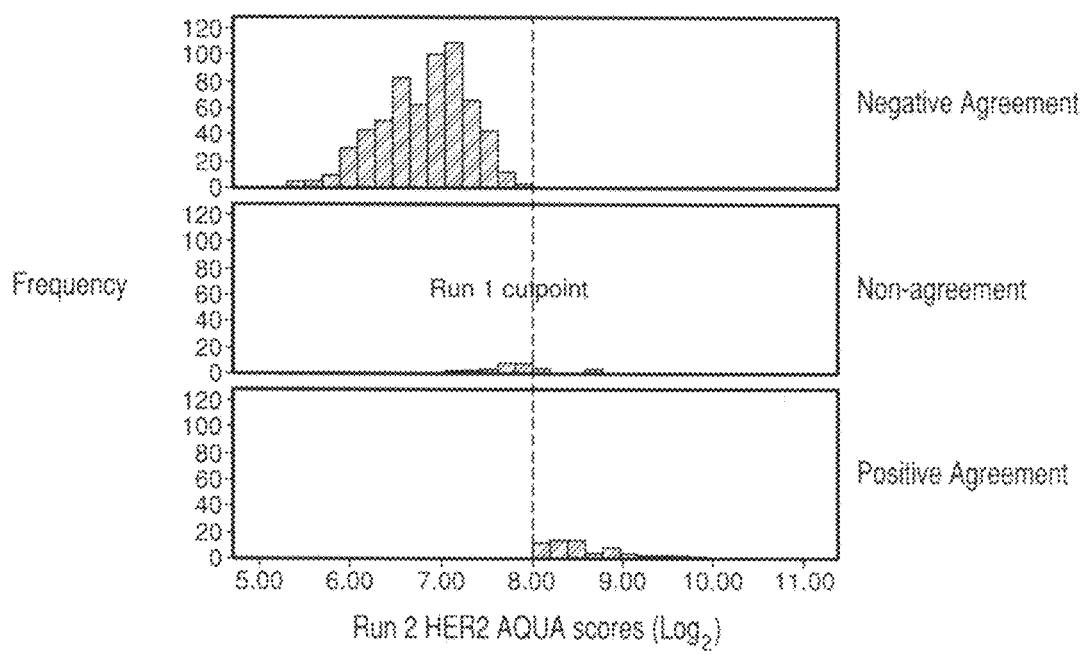

To assess where differential classification occurred in the distribution of normalized AQUA® scores, paneled frequency histograms were generated to examine where differentially classified cases were occurring. As shown in FIG. 7, for instrument-to-instrument, operator-to-operator and run-to-run, differentially classified cases occur at the cut-point and not over the entire distribution. These data suggest that the classification error concerns cut-point selection not generation and reproducibility of the normalized HER2 AQUA® score. Taken together, these data show classification of patients for inter-instrument, inter-operator, and inter-run assessment of HER2 expression using AQUA® scoring is highly reproducible with concordance rates approaching, if not exceeding, that suggested by ASCO/CAP.

Example 2

AQUA® Analysis of EGFR: Analytical Performance Data

Figure 8A:
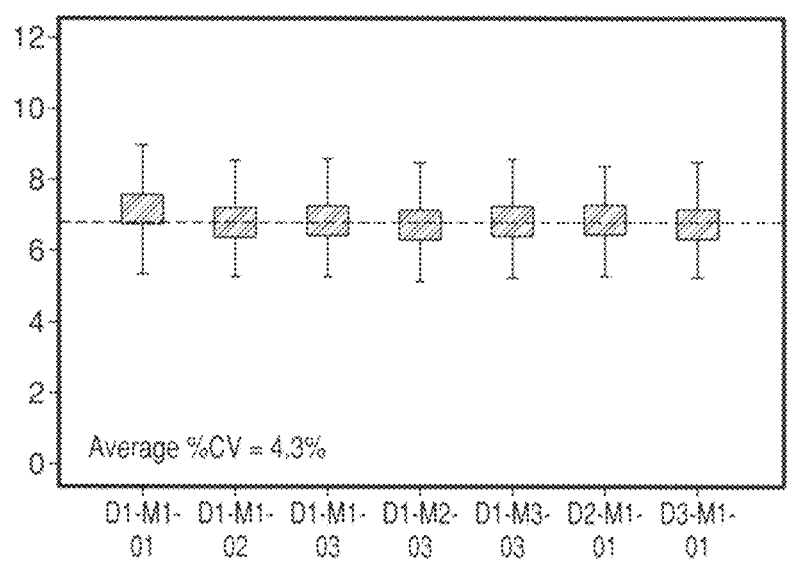
FIGS. 8A-D illustrate the analytical performance of AQUA® analysis and EGFR assay. (A) Box plot of log(2) transformed AQUA® scores of HER2 for 748 cases across 3 staining days (D), machines (M), and operators (O) with indicated % CV. (B). Linear regression analysis for EGFR AQUA® scores generated on test array of breast tumor, normal and cell line controls (n=152) across 3 slides and 3 staining days with indicated average R values and slopes. (C) Box plot of $log_2$ transformed AQUA® scores of EGFR for 40 tumors from (B) with indicated % CV. (D) Box plot of $log_2$ transformed AQUA® scores of EGFR for 35 cell lines (2× redundant) from (B) with indicated % CV.
Figure 8B:
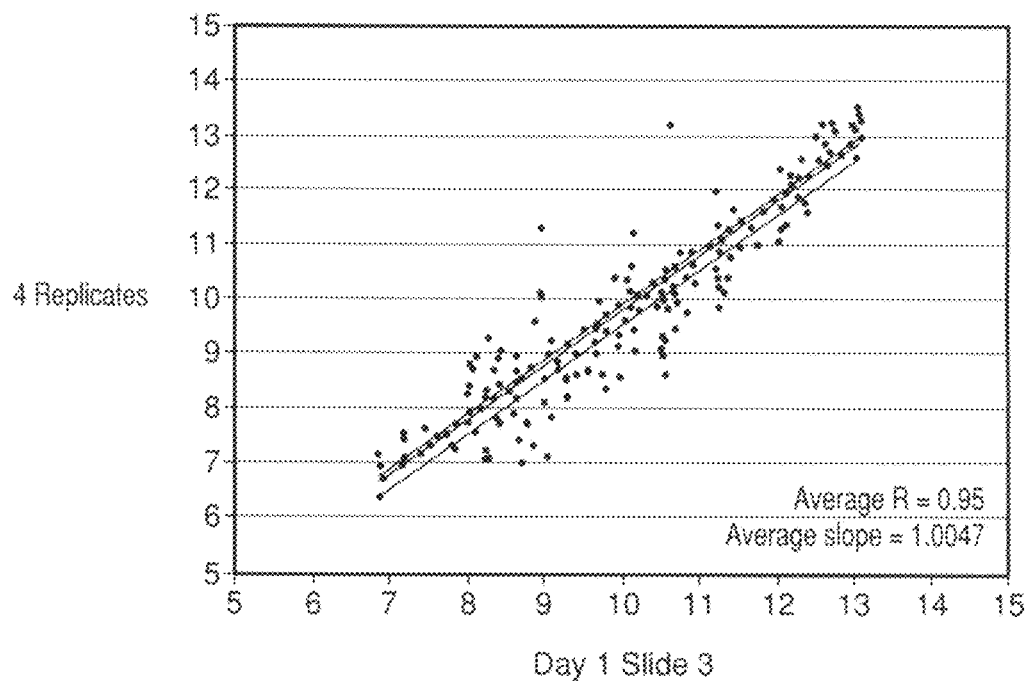
Figure 8C:
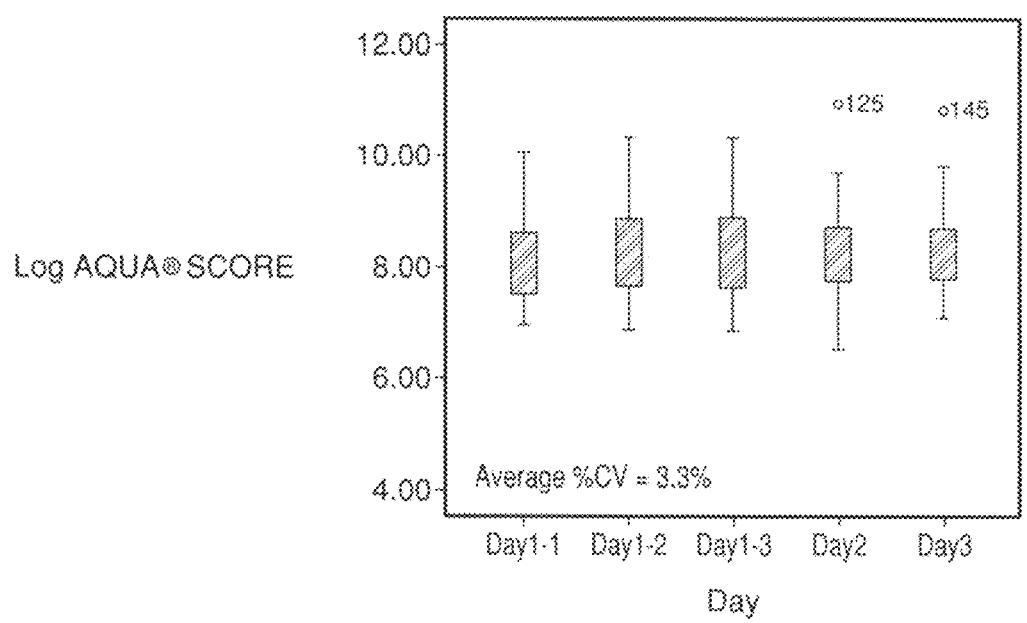
Figure 8D:
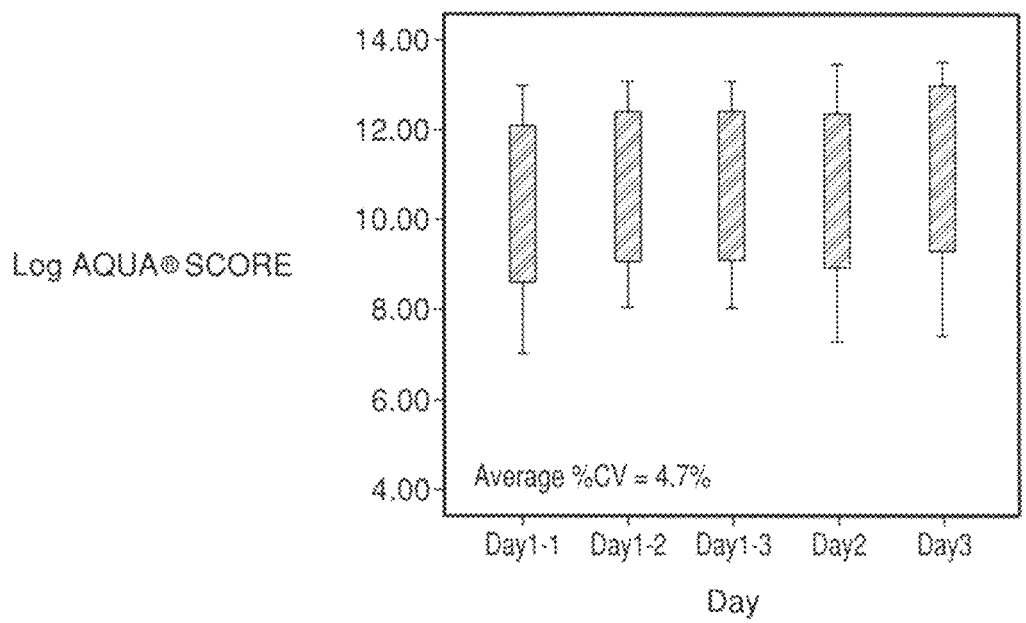

The methods of the present invention were applied to the evaluation of the biomarker EGFR in breast cancer tissue sections. As shown in FIG. 8A, a TMA cohort of 748 specimens was analyzed for HER2 expression by normalized AQUA® analysis across three instruments, 3 operators, and 3 separate staining runs with an average % CV of 4.3%. Preliminary analytical performance assessment was performed with EGFR PharmDx (Dako). As FIGS. 8B-D demonstrate, AQUA® analysis of EGFR expression across 3 slides and 3 staining days on a TMA composed of breast tumor and cell lines (n=152) shows a high degree of precision slide-to-slide and day-to-day with an average slope of 1.00047, an average Pearson's R of 0.95, an average % CV for tumor tissue of 3.3%, and an average % CV for cell lines of 4.7%. Taken together, these data demonstrate that AQUA® analysis allows for an EGFR assay with a high degree of precision, and combined with instrument and software controls, development of a robust clinical biomarker assay is possible.

Example 3

AQUA® Analysis of ER Expression: Reproducibility

To demonstrate reproducibility of AQUAnalysis™ with another biomarker, four breast tissue blocks were obtained that represent a range of estrogen receptor (ER) expression (as judged by Allred scoring). Sections of these tissue blocks were then taken to generate H&E slides on which a board certified pathologist circled the area of tumor for all subsequent analyses. A serial set of sections was DAB stained with the monoclonal mouse anti-human estrogen receptor α, clone 1D5 antibody and evaluated for Allred scoring by the same pathologist. See, e.g., Harvey J M, et al., (1999) J. Clin. Oncol. 12:1474, which is hereby incorporated by reference in its entirety.

Serial sections were then stained using the immunofluorescence staining protocol described above. Images were collected on the HistoRx PM-2000™ microscopy platform and then passed to AQUAnalysis™ for scoring. All scores were transformed on a log 2 scale.

Image files for the four slides were acquired and then passed through the AQUAnalysis™ software package n=10 times by the same operator to demonstrate overall software reproducibility. For all files, the % CV was essentially 0 (less then 1E−7).

The same four image files were then provided to three different operators along with the software operating instructions. Here, the operators redacted images in the method outlined for technician review of image quality, which reflects typical use. The results, shown in Table 1, demonstrate that even with more than 30% variability in the number of images scored (in the case of slides #3 and #4) the % CV in the overall score is still on the order of 1% or less.

TABLE 1

| | | Inter-operator reproducibility | | | | |
|---|---|---|---|---|---|---|
| (n = 3) | Operator | Mean AQUA ® score per operator | #fields scored | Mean | StDev | % CV |
| Slide #1 | Operator 1 | 9.941 | 100 | 9.945 | 0.0047 | 0.05 |
| | Operator 2 | 9.945 | 104 | | | |
| | Operator 3 | 9.950 | 109 | | | |
| Slide #2 | Operator 1 | 10.382 | 60 | 10.397 | 0.0357 | 0.34 |
| | Operator 2 | 10.437 | 61 | | | |
| | Operator 3 | 10.370 | 62 | | | |
| Slide #3 | Operator 1 | 10.254 | 102 | 10.232 | 0.0194 | 0.19 |

TABLE 1-continued

Inter-operator reproducibility

| (n = 3) | Operator | Mean AQUA ® score per operator | #fields scored | Mean | StDev | % CV |
|---|---|---|---|---|---|---|
| | Operator 2 | 10.216 | 110 | | | |
| | Operator 3 | 10.227 | 150 | | | |
| Slide #4 | Operator 1 | 13.723 | 4 | 13.818 | 0.1644 | 1.19 |
| | Operator 2 | 13.723 | 4 | | | |
| | Operator 3 | 14.008 | 14 | | | |

To demonstrate performance at independent sites and using alternative hardware systems for image acquisition, the AQUAnalysis™ software was evaluated on three different platforms which meet the required hardware specifications (described in the operator's manual). The systems are described below in Table 2.

TABLE 2

Hardware systems used for reproducibility testing

| | System 1 | System 2 | System 3 |
|---|---|---|---|
| Component | HistoRx PM-2000 ™ | External System #1 | External System #2 |
| Light Source | Exfo Xcite 120 | Exfo Xcite 120 | Prior Lumen |
| Microscope | Olympus BX-52 | Olympus BX-51 | Nikon 50i |
| Objective Mag. | 20× | 10× | 10× |
| Camera | Optronics Quantifire, 2048 × 2040, 7.4 µM pixel | Cooke Sensicam QE 1376 × 1040, 6.45 µM pixels | PixelLink PL-B872-MF 1392 × 1040, 6.45 µM pixels |
| FOV size | 758 µM × 758 µM | 887 µM × 671 µM | 898 µM × 671 µM |
| Filters | Cy3, Cy5, DAPI | Cy3, Cy5, DAPI | Cy3, Cy5, DAPI |

To assure uniform testing, it was critical to assure that the same regions of tissue were sampled on each system since automated image acquisition is not required or necessarily available on all listed platforms. To accomplish this, a TMA was constructed from the same four samples described in the previous reproducibility tests, using five cores from each of the four blocks (for a total of 20 spots). This microarray was then immunofluorescently stained and the same single TMA was acquired on three separate hardware systems sequentially. Images were acquired in the laboratory of the installed hardware system by the operator after receiving training on the software operation. Results were maintained in a blinded manner for all external testing and are provided below in Table 3.

TABLE 3

Results of inter-site/inter-hardware testing

| | HistoRx | | | External Site 1 | | | External Site 2 | | | Overall | | |
|---|---|---|---|---|---|---|---|---|---|---|---|---|
| | AVG | SD | CV | AVG | SD | CV | AVG | SD | CV | AVG | SD | CV |
| Sample 1 | 8.12 | 0.19 | 2.40 | 9.01 | 0.40 | 4.44 | 8.36 | 0.45 | 5.34 | 8.50 | 0.46 | 5.37 |
| Sample 2 | 9.05 | 0.55 | 6.10 | 9.72 | 0.52 | 5.36 | 8.74 | 0.81 | 9.22 | 9.17 | 0.51 | 5.51 |
| Sample 3 | 9.34 | 0.16 | 1.66 | 10.08 | 0.04 | 0.39 | 9.40 | 0.31 | 3.26 | 9.61 | 0.41 | 4.27 |
| Sample 4 | 12.01 | 0.30 | 2.53 | 12.78 | NA | NA | 11.23 | 0.57 | 5.11 | 12.01 | 0.77 | 6.43 |

Each 'sample' refers to the average of the scores from the five-fold redundant TMA spots cored from the associated whole tissue section sample used in previous testing (with a range of Allred scores).

Overall, the % CV values for mean AQUAS score values are in the 4-6.5% range and do not vary significantly across the range of ER expression. The % CV variations observed within a single sample at a single site is the result of indicative of marker heterogeneity within the sample, not measurement error. ANOVA analysis indicated that while there is significant variation between the samples scores as expected ($p<0.001$), there is no significant difference between sites ($p=0.58$).

Example 4

AQUAS Analysis of ER Expression: Correlation with Allred Scoring

To demonstrate the utility of AQUA® scores, a comparison study was performed to examine the relationship between breast tissue immunofluorescently stained then scored using AQUAnalysis™ and breast tissue chromogencially stained then scored using the Allred method. As discussed in Example 1, a tissue microarray cohort of 669 patients was obtained from the Yale University Tissue Microarray Facility consisting of samples from the Yale University Department of Pathology tissue archives collected between 1961 and 1983.

Figure 9A:
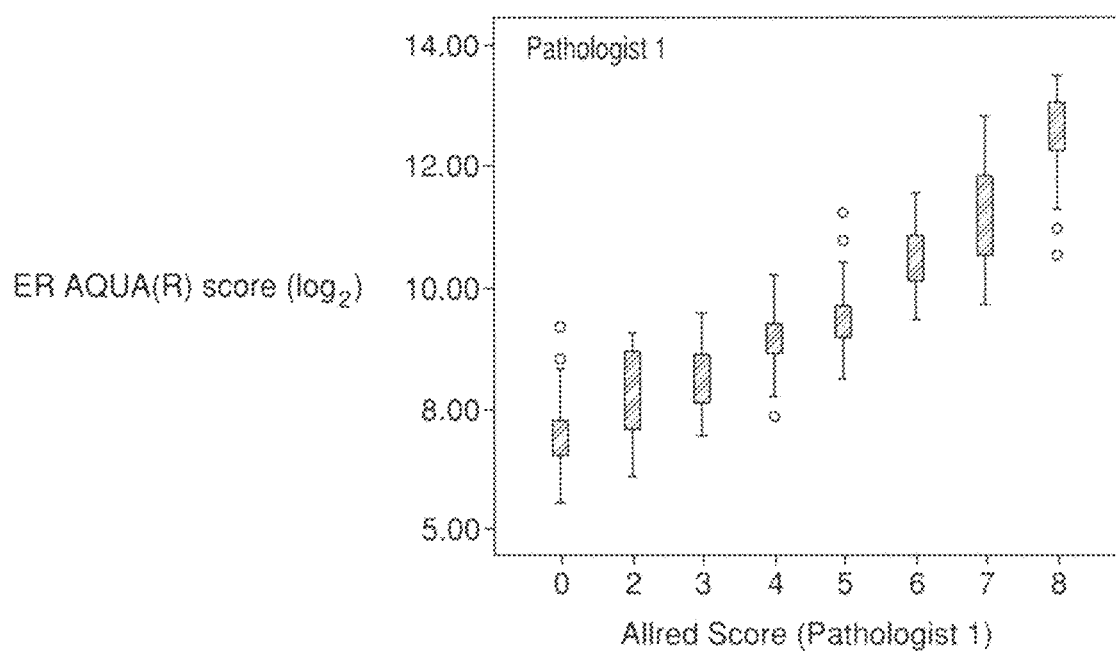
Figure 9B:
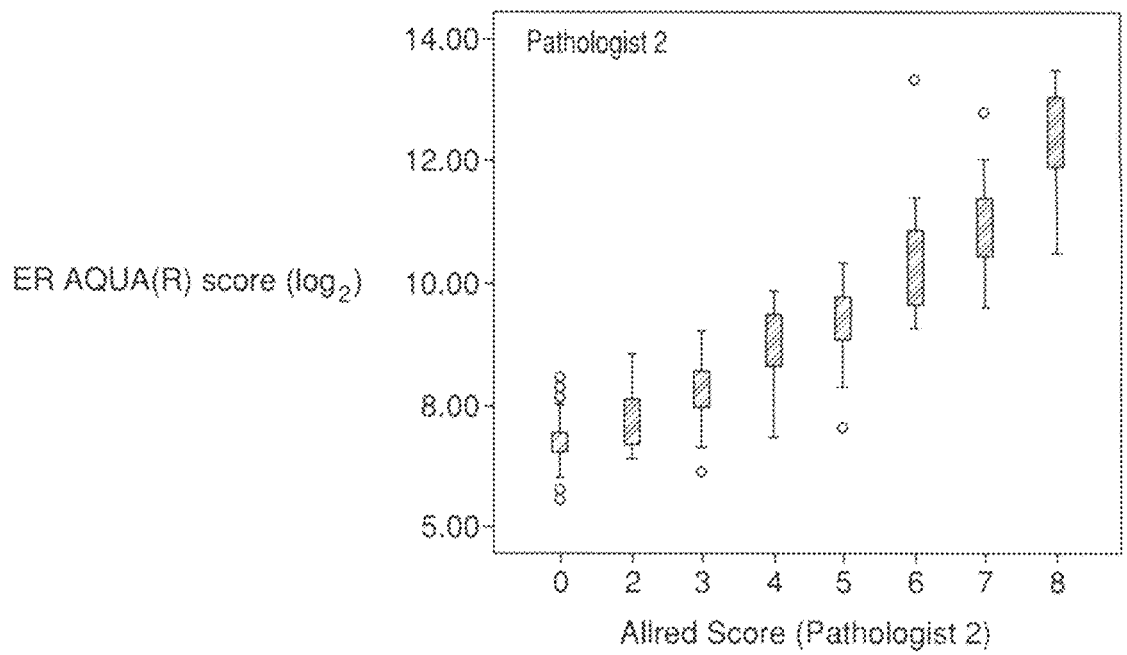
Figure 9C:
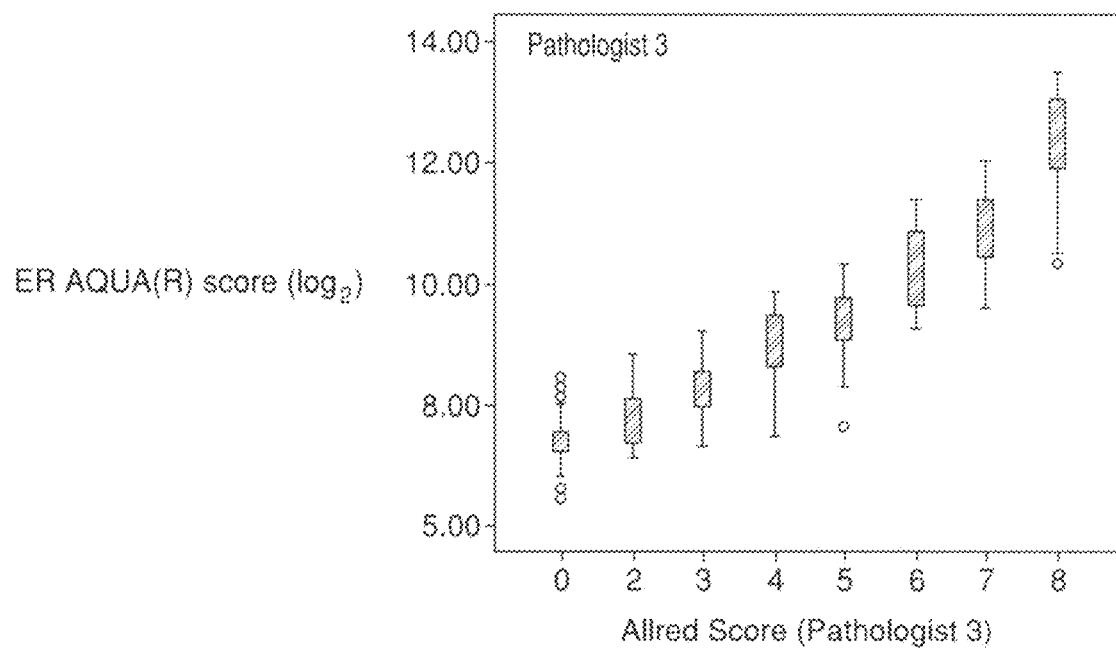

Two serial sections were stained using the mouse monoclonal 1D5 antibody. One section was stained using DAB and the second using the immunofluorescence methods described above above. The DAB stained slide was then provided to three board certified pathologists for Allred scoring. Each pathologist was blinded to the results of the others (and to the fluorescent staining results) and no further information was given other than the nature of the tissue being scored and the biomarker (ER). In parallel the fluorescently stained serial section of the TMA was run through the AQUAnalysis™ software and AQUA® scores were generated. There was a definitive trend between Allred scoring and AQUA® scoring as demonstrated below (FIGS. 9A-C)) for all pathologists.

Figures 9D, 10A:
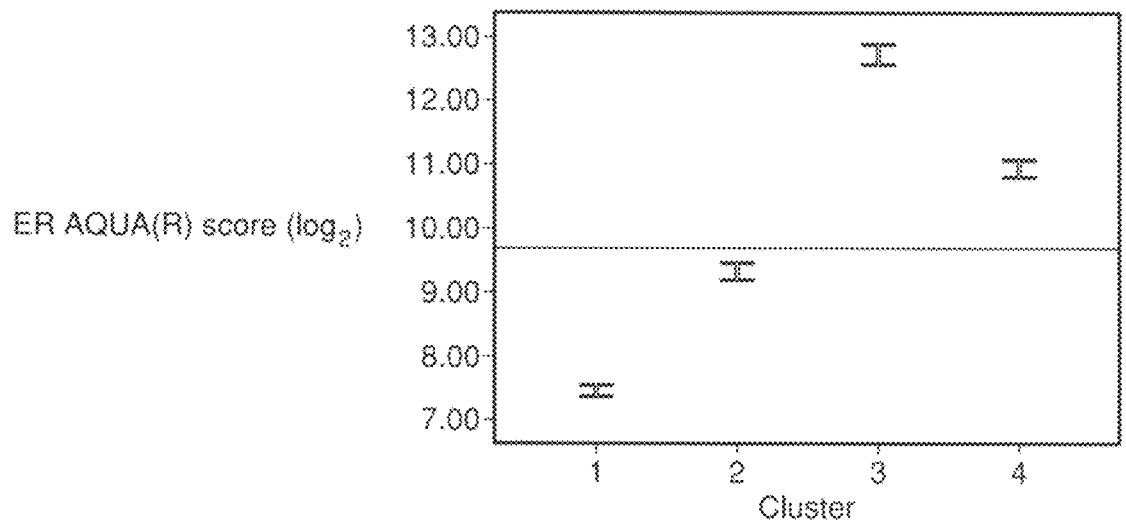

Allred scoring and AQUA® scoring was highly correlative (p<0.001) for all pathologists by non-parametric correlation analysis (Spearman's Rho, FIG. 9D). Multinomial logistic regression analysis demonstrated a significant (p<0.001) and direct (pseudo $R^2$) relationship between Allred scoring and AQUA® scoring for all pathologists (see FIG. 9).

Although there is variation in the individual scores provided by the pathologists, in typical practice, a cut point is applied to the data. For the Allred scoring method, a cut point of 3 was used such that scores <3 (0 or 2) were considered negative and scores ≥3 were considered positive. See, e.g., Harvey et al, supra. This cut point was applied to the individual results of each of the manually scored pathologist data sets and a consensus score was generated. Samples where at least one pathologist could not provide a score were eliminated from the consensus. If scores did not agree, the majority score was used. As a result of this, it was observed that pathologists demonstrated universal agreement for positive/negative classification 91% of the time for 523 cases.

To determine a cut point for the AQUA® score data, an unsupervised Bayesian clustering algorithm based on log-likelihood distances was applied using the commercially available software program, SPSS(SPSS, Inc. Chicago, Ill). For this algorithm, patients were grouped based on cluster membership of AQUA® scores. When the clustering was performed, four clusters are manifested in the data (see FIG. 10A). Analogous to Allred scoring, survival was used to determine positive and negative classification between expression groups. As shown in FIG. 10B, three (clusters 2-4) show improved survival whereas cluster 1 show decreased survival. Therefore, patients in cluster 1 were considered ER negative and all others ER positive.

With positive/negative classification determined for the AQUA® data, a concordance matrix was generated to compare the results of the AQUAnalysis™ software with the results of the scoring consensus derived from manual Allred scoring. The results indicate that the overall concordance between the methods is 94.9% with percent positive agreement of 96.0% and percent negative agreement of 92.5%, as shown in Table 4 below.

TABLE 4

Concordance of AQUA ® scoring with manual IHC Allred scoring.

| | | Manual Allred Scoring | | |
| --- | --- | --- | --- | --- |
| | | Positive | Negative | Total |
| AQUA ® scoring | Positive | 218 | 8 | 226 |
| | Negative | 9 | 99 | 108 |
| | Total | 227 | 107 | 334 |

% Positive agreement (218/227) = 96.0% (95% CI = 92.6-98.2)
% Negative agreement (99/107) = 92.5% (95% CI = 85.8-96.7)
% Total agreement (317/334) = 94.9% (95% CI = 92.0-97.0)

Figure 11A:
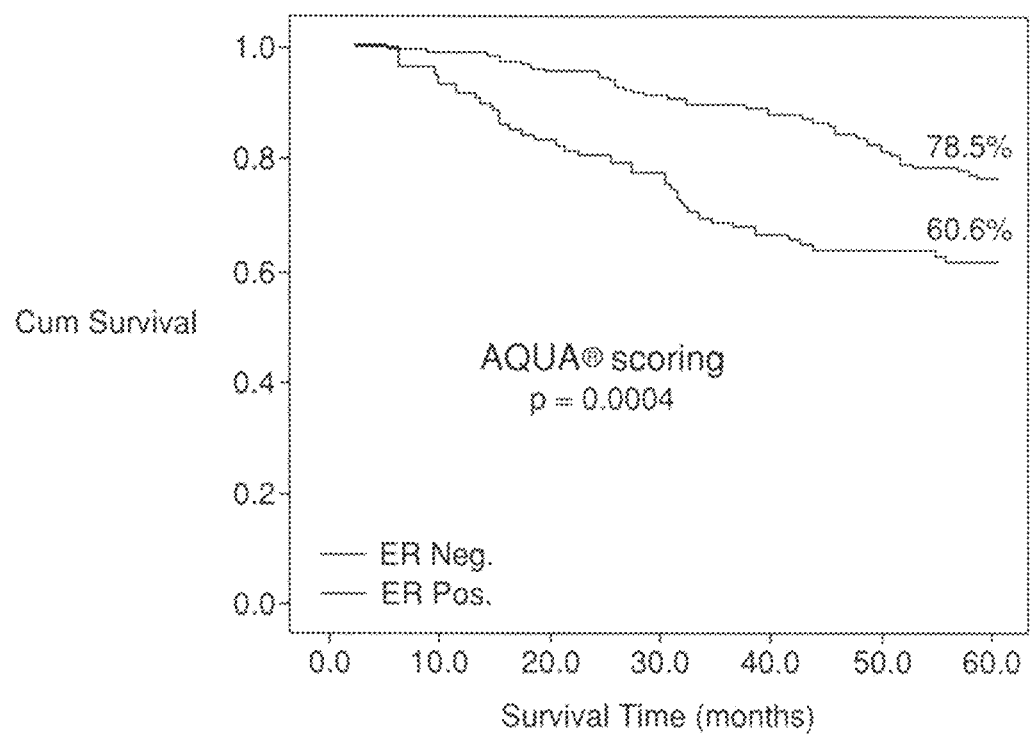
FIGS. 11A-B compare the five year disease specific survival using the Allred scoring (A) and AQUA® scoring (B).
Figure 11B:
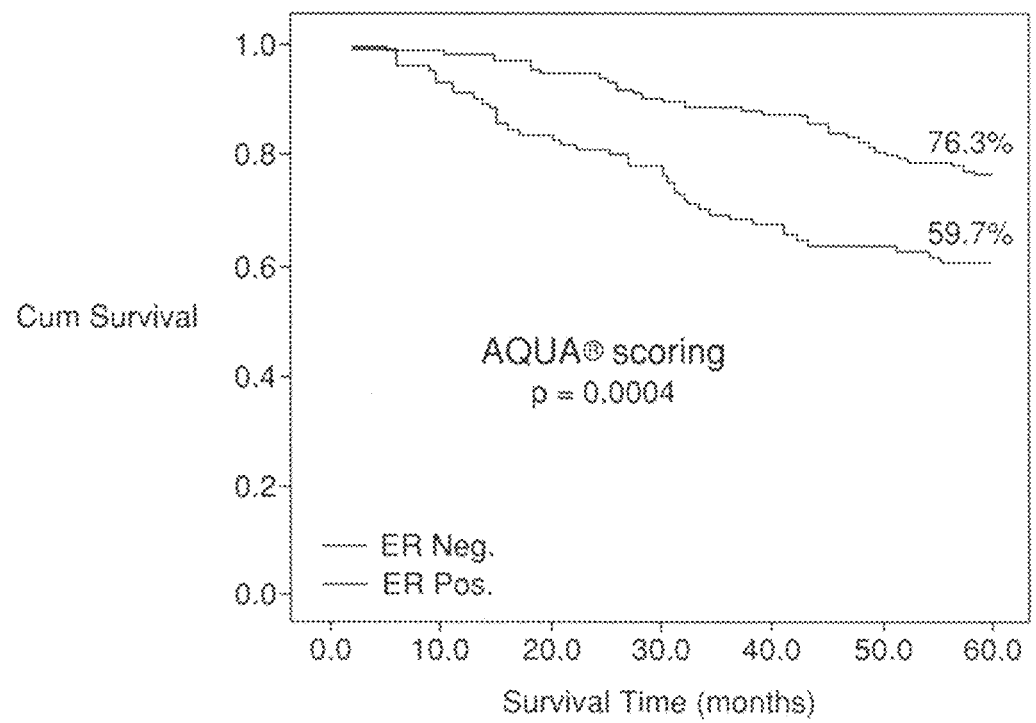

As confirmation of positive/negative classification of ER AQUA® scores, overall survival was compared between Allred scoring and AQUA® scoring, as shown in FIG. 11. Both methods predict significant five-year disease specific survival and show similar cumulative survival rates for positive/negative classification.

Example 5

Reproducibility of AQUA® Scoring and Allred Scoring

Figure 12A:
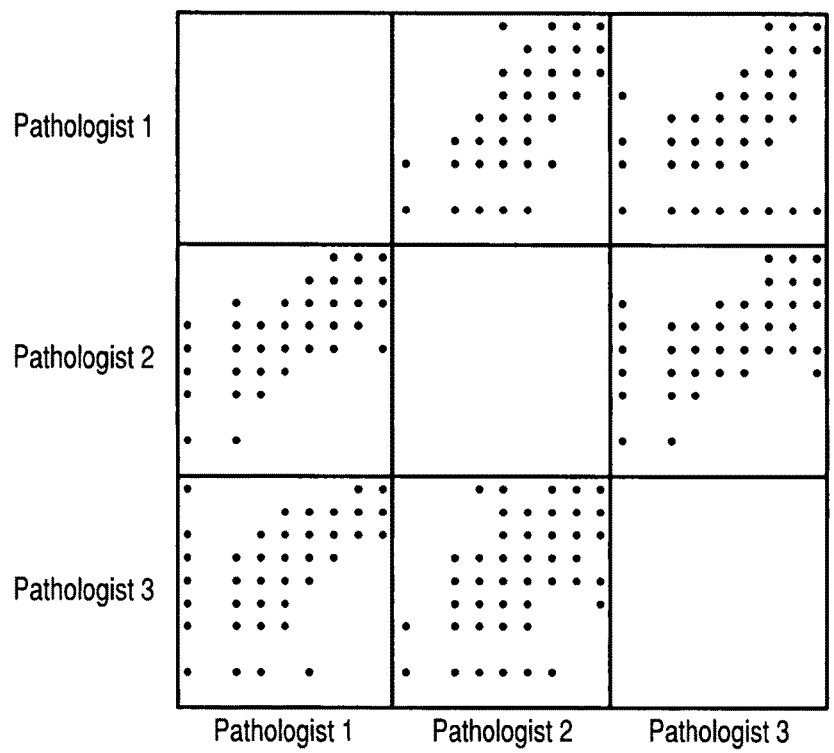
FIGS. 12A-B illustrates the comparison of ER expression scores determined by 3 pathologists reading the same TMA slide using the Allred score method (A) and the comparison of ER expression AQUA scores determined by 3 PM-2000 instruments reading the same TMA slide (B).
Figure 12B:
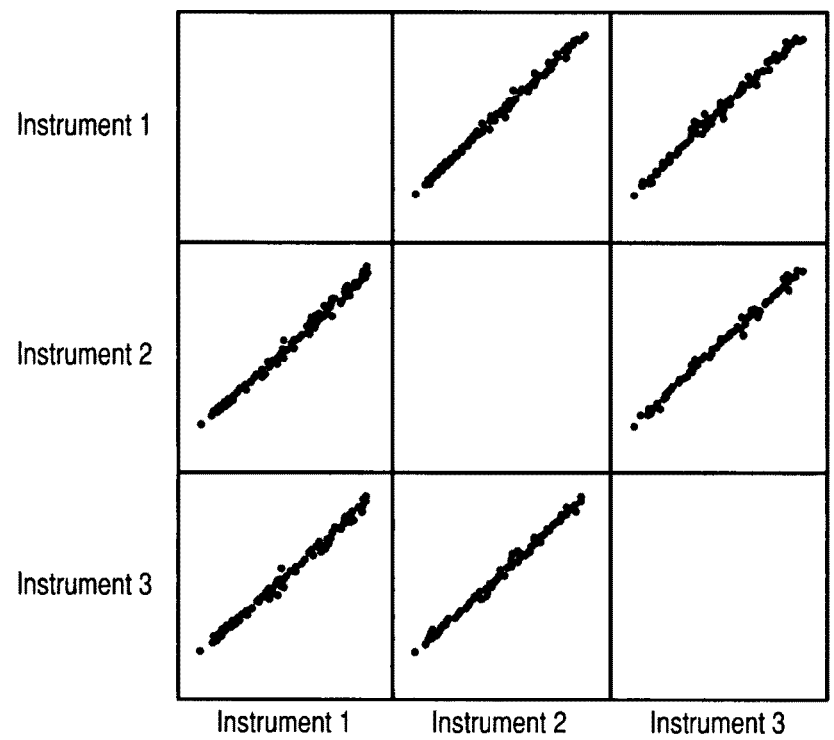

A single TMA slide described in Examples 3 and 4 was stained for ER expression using conventional chromogenic immunohistochemistry techniques as previously described and independently evaluated by three pathologists using light microscopy and scored by the Allred method (FIG. 12A). A second, serial section, TMA slide was stained for AQUA® analysis (fluorescent immunohistochemistry) of ER expression and the same slide was analyzed on three independent instruments by AQUA® analysis (FIG. 12B). Examination of the results obtained by each pathologist vs. each other pathologist shown as scatterplots (FIG. 12A) shows that while overall concordance is high, there are samples considered positive by one pathologist that are considered negative by another. These patients would receive different treatment (hormonal therapy) depending on which pathologist read their ER results.

The kappa values (which range from 0 to 1, Table 5) over the spread of Allred scores indicate that there is a great deal of variance in the respective pathologists manual scoring determinations.

TABLE 5

Kappa of results scored by pathologists.

Path 1 v. Path 2: Kappa = 0.482 (p < 0.001)
Path 1 v. Path 3: Kappa = 0.444 (p < 0.001)
Path 2 v. Path 3: Kappa = 0.400 (p < 0.001)

Overall regression analysis of the results obtained for each combination of PM 2000 instruments is shown in FIG. 12B. There is extremely high correlation (R2>0.99 in all cases, Table 6) with a strong correspondence (regression coefficients, analogous to the slop eof the regression line, are all ~1.0). Furthermore, ANOVA analysis of the datasets produces p>0.05, indicating that the data sets are statistically indistinguishable. In comparison to FIG. 12A, results obtained by AQUA analysis is highly reproducible with an average CV of 1.35%. Therefore the methods of the present invention provide for consistent results regardless of which instrument (and therefore location) the sample was analyzed on.

TABLE 6

Comparison of results obtained on three instruments by AQUA analysis.

| Comparison | $R^2$ | Regression Coefficient (95% CI; p value) |
| --- | --- | --- |
| Instrument 1 v2 | 0.996 | 1.003 (0.99-1.01; <0.001) |
| Instrument 1 v3 | 0.995 | 1.01 (1.00-1.02; <0.001) |
| Instrument 2 v3 | 0.996 | 1.003 (0.99-1.01; <0.001) |

The Examples are provided for illustrative purposes only and should not be used to limit the scope of the invention. Many other embodiments of the invention are apparent to those of ordinary skill in the art in view of the contents and teachings of this disclosure.

What is claimed is:

1. A method of reproducibly quantifying biomarker expression in a slide-mounted tissue sample, the method comprising:
   (a) obtaining a slide-mounted tissue sample, which has been stained to permit localization of at least one cellular compartment and at least one biomarker;
   (b) obtaining one or more pixel-comprised images of the stained tissue sample using a microscope, and analyzing the one or more pixel-comprised images to obtain one or more data sets;

(c) automatically analyzing the one or more data sets derived from the image pixels to differentiate data signal from noise;

(d) automatically analyzing the one or more data sets derived from the image pixels to differentiate data signal attributable to each of said at least one cellular compartment;

(e) optionally automatically analyzing the one or more data sets derived from the image pixels to differentiate data signal attributable to said at least one biomarker for each of said at least one cellular compartment;

(f) quantifying the amount of biomarker expressed in each of said at least one cellular compartment to arrive at a standardized score, which is a product of a raw score and one or more factors selected from the group consisting of a calibration cube factor, a light source factor and an optical path factor, whereby a run comprises steps (a)-(f), and the biomarker expression in the same slide-mounted tissue sample is quantified in a manner having a level of reproducibility above 80 percent for separate runs, in which each automatic analysis step is carried out in an unsupervised manner and comprises an unsupervised pixel-based clustering algorithm, and whereby the microscope allows for automatic adjustment of exposure time to provide an optimized dynamic range of data captured in the image pixels.

2. The method of claim 1 in which the light source factor reduces variability in intensity of the light source.

3. The method of claim 1 in which data signal attributable to two or more cellular compartments is differentiated.

4. The method of claim 1 in which the amount of biomarker expressed in each of two or more cellular compartments is quantified.

5. The method of claim 1 in which data signal attributable to two or more cellular compartments is differentiated with a confidence interval of about 95%.

6. The method of claim 1 which further comprises assessing the image quality of the one or more slide-mounted tissue samples, the one or more pixel-comprised images or one or more magnified portions thereof, by testing any one of signal integrity, sample integrity and image integrity of the slide mounted sample and removing the image from analysis if one or more of the signal integrity, sample integrity and image integrity fail.

7. The method of claim 1 which provides a greater than 85% concordance for sample classification from one run to another.

8. The method of claim 1 which provides a greater than 90% concordance for sample classification from one run to another.

9. The method of claim 1 which provides a quantified measure of biomarker expression having a level of reproducibility above 90 percent.

10. The method of claim 1 which provides a quantified measure of biomarker protein expression having a level of reproducibility above 95 percent.

11. The method of claim 1 which provides a quantified measure of biomarker expression having a level of reproducibility falling in the range of about 90 to about 97 percent.

12. The method of claim 1 which provides a quantified measure of biomarker expression having a coefficient of variation (% CV) below 20 percent.

13. The method of claim 1 which provides a quantified measure of biomarker expression having a coefficient of variation (% CV) below 10 percent.

14. The method of claim 1 which provides a quantified measure of biomarker expression having a coefficient of variation (% CV) below 5 percent.

15. The method of claim 1 which provides a quantified measure of biomarker expression having a coefficient of variation (% CV) falling in the range of about 4 to about 7 percent.

16. The method of claim 1 in which the slide-mounted tissue sample has been stained with an optimal dilution of one or more reagents.

17. The method of claim 16 in which said optimal dilution produces one or more pixel-comprised images having an optimal dynamic range metric.

18. A non-transitory computer readable medium having computer readable instructions stored thereon for execution by a processor to perform a method of reproducibly quantifying biomarker expression in a slide-mounted tissue sample comprising:

(a) acquiring one or more pixel-comprised images of a slide-mounted tissue sample, which has been stained to permit localization of at least one cellular compartment and at least one biomarker and analyzing the one or more pixel-comprised images to obtain one or more data sets;

(b) automatically analyzing the one or more data sets to differentiate data signal from noise;

(c) automatically analyzing the one or more data sets to differentiate data signal attributable to each of said at least one cellular compartment; and (d) quantifying the amount of biomarker expressed in each of said at least one cellular compartment to arrive at a standardized score, which is a product of a raw score and one or more factors selected from the group consisting of a calibration cube factor, a light source factor and an optical path factor, whereby a run comprises steps (a)-(d), and the biomarker expression in the same slide-mounted tissue sample is quantified in a manner that is reproducible for separate runs, in which each automatic analysis step is carried out in an unsupervised manner and comprises an unsupervised pixel-based clustering algorithm, and whereby a microscope allows for automatic adjustment of exposure time to provide an optimized dynamic range of data captured in the image pixels.

19. The non-transitory computer readable medium of claim 18 in which the computer readable instructions stored thereon for execution by a processor further comprises instructions to perform a method that includes, prior to said quantifying step, an optional step of automatically analyzing the one or more data sets derived from the image pixels to differentiate data signal attributable to said at least one biomarker for each of said at least one cellular compartment.

20. A system for reproducibly quantifying biomarker expression in a slide-mounted tissue sample comprising:

(a) one or more lenses configured to magnify at least a portion of a slide-mounted tissue sample, which has been stained to permit localization of at least one cellular compartment and at least one biomarker;

(b) a microscope, including a light source and an image sensor in optical communication with said one or more lenses, the microscope obtaining one or more pixel-comprised images of the stained tissue sample;

(c) a processor in communications with the microscope, configured to analyze the one or more pixel-comprised images to obtain one or more data sets; and then (i) automatically analyze the one or more data sets to differentiate data signal from noise, (ii) automatically analyze the one or more data sets to differentiate data signal attributable to each of said at least one cellular compartment, and (iii) quantify the amount of biomarker expressed in each of said at least one cellular compartment to arrive at a standardized score, which is a product of a raw score and one or more factors selected from the group consisting of a calibration cube factor, a light source factor and an optical path factor, whereby a run comprises steps (i)-(iii), and the biomarker expression in the same slide-mounted tissue sample is quantified in a manner that is reproducible for separate runs, in which each automatic analysis step is carried out in an unsupervised manner and comprises an unsupervised pixel-based clustering algorithm, and whereby the microscope allows for automatic adjustment of exposure time to provide an optimized dynamic range of data captured in the image pixels.

21. The system of claim 20 in which the processor is further configured to optionally automatically analyze the one or more data sets derived from the image pixels to differentiate data signal attributable to said at least one biomarker for each of said at least one cellular compartment.

* * * * *